(12) United States Patent
Lambert et al.

(10) Patent No.: US 9,066,951 B2
(45) Date of Patent: Jun. 30, 2015

(54) DRUGS TO TREAT HPV INFECTION

(75) Inventors: Paul F. Lambert, Madison, WI (US);
Paul G. Ahlquist, Madison, WI (US);
Dohun Pyeon, Greenwood Village, CO (US); Hao Shun Huang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 273 days.

(21) Appl. No.: 12/994,592

(22) PCT Filed: May 29, 2009

(86) PCT No.: PCT/US2009/045680
§ 371 (c)(1),
(2), (4) Date: Feb. 25, 2011

(87) PCT Pub. No.: WO2009/148961
PCT Pub. Date: Dec. 10, 2009

(65) Prior Publication Data
US 2011/0165220 A1    Jul. 7, 2011

Related U.S. Application Data

(60) Provisional application No. 61/130,270, filed on May 29, 2008.

(51) Int. Cl.
*A01N 43/64* (2006.01)
*A61K 31/53* (2006.01)
*A61K 31/166* (2006.01)
*A61K 31/167* (2006.01)
*A61K 9/00* (2006.01)

(52) U.S. Cl.
CPC .............. *A61K 31/53* (2013.01); *A61K 9/0031* (2013.01); *A61K 9/0034* (2013.01); *A61K 31/166* (2013.01); *A61K 31/167* (2013.01)

(58) Field of Classification Search
USPC ........................................................ 514/243
See application file for complete search history.

(56) References Cited

U.S. PATENT DOCUMENTS

| | | |
|---|---|---|
| 5,605,919 A | 2/1997 | Matsumori |
| 6,498,178 B2 | 12/2002 | Stamos et al. |
| 6,541,472 B1 | 4/2003 | Pevear et al. |
| 6,720,346 B2 | 4/2004 | Chu et al. |
| 7,183,316 B2 | 2/2007 | Dannenberg et al. |
| 7,563,597 B2 | 7/2009 | Ahlquist et al. |
| 7,824,383 B2 | 11/2010 | Sokal et al. |

OTHER PUBLICATIONS

Fields et al, Fields Virology: vol. 2, Third Edition, Lippincott-Raven Publishers, pp. 2077-2101 (1996).*
Tota et al, Epidemiology and Burden of HPV Infection and Related Diseases: Implications for Prevention Strategies, Preventive Medicine, vol. 53, Supplement 1, pp. S12-S21 (2011).*
Culp et al, "Quantitative RT-PCR Assay for HPV Infection in Cultured Cells," Journal of Virological Methods, vol. 111, Issue 2, pp. 135-144 (2003).*
Pyeon, D., et al., Production of Infectious Human Papillomavirus Independently of Viral Replication and Epithelial Cell Differentiation, PNAS, 2005, 102(26):9311-9316.
Pyeon, D., et al., Establishment of Human Papillomavirus Infection Requires Cell Cycle Progression, PLoS Pathogens, 2009, 5(2):e1000318, 9 pages.
Zhang, J., et al., A Simple Statistical Parameter for Use in Evaluation and Validation of High Throughput Screening Assays, Journal of Biomolecular Screening, 1999, 4(2)67-73.
PCT International Preliminary Report on Patentability, Application No. PCT/US2009/045680, Dec. 9, 2010.
U.S. Appl. No. 11/454,604, Vaginal Drug Delivery System and Method, filed Jun. 16, 2006.
International Search Report under date of mailing of Oct. 16, 2009 in connection with PCT/US2009/045680.

* cited by examiner

*Primary Examiner* — Dennis J Parad
(74) *Attorney, Agent, or Firm* — Quarles & Brady LLP

(57) ABSTRACT

A method of inhibiting HPV virus infection is disclosed. In one embodiment, the method involves exposing a papillomavirus to an effective amount of a compound selected from the group consisting of Compound 13, Compound 14, and analogs of Compounds 13 and 14. In another embodiment, the method involves administering an inhibitor selected from the group consisting of Compound 13, Compound 14, and analogs of Compounds 13 and 14 to a susceptible tissue or cell.

7 Claims, 14 Drawing Sheets

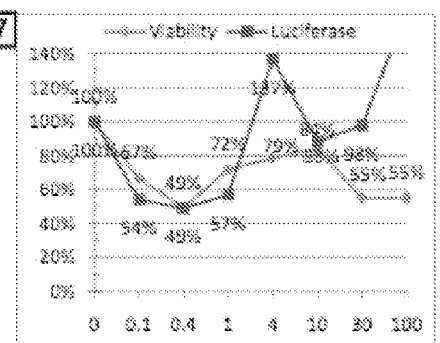
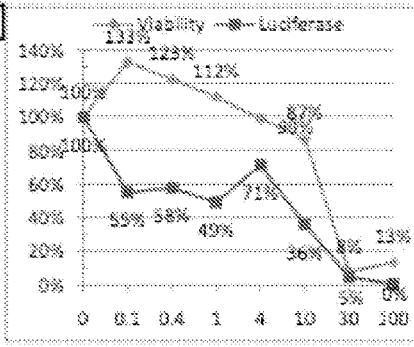
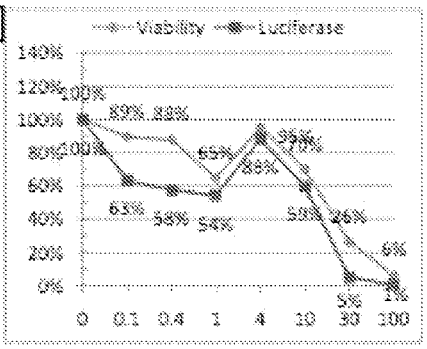
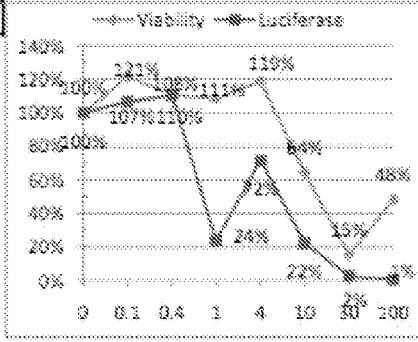
Figure 2 CON [1]

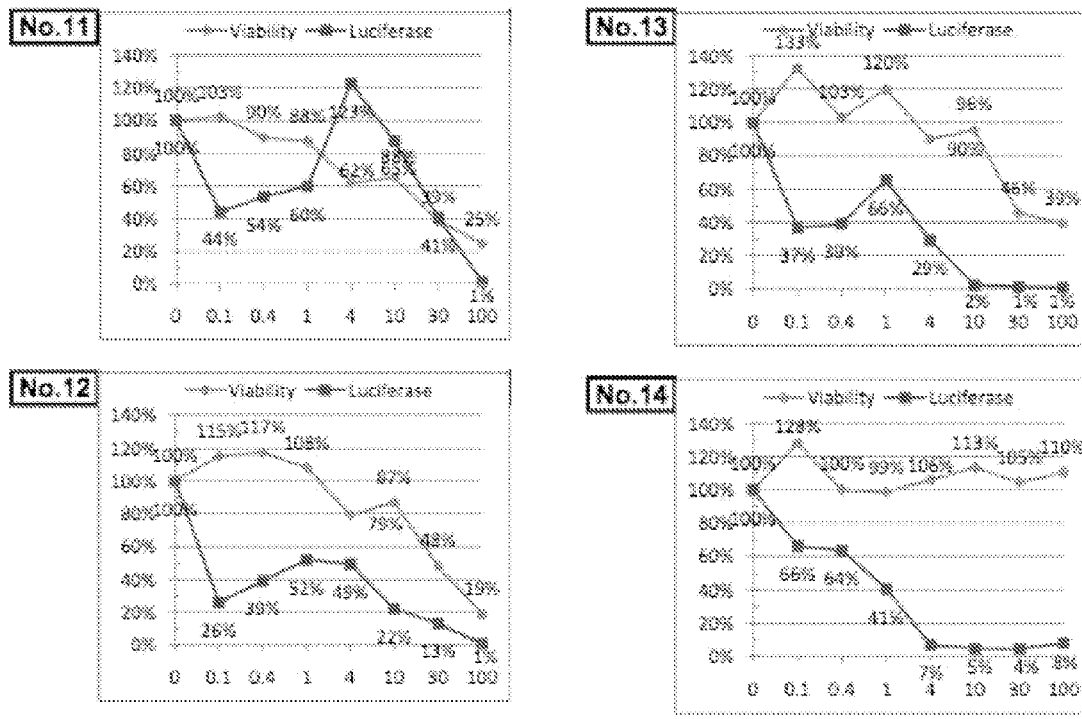
Figure 2 CON [2]

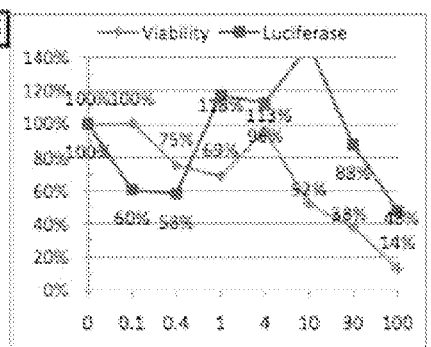
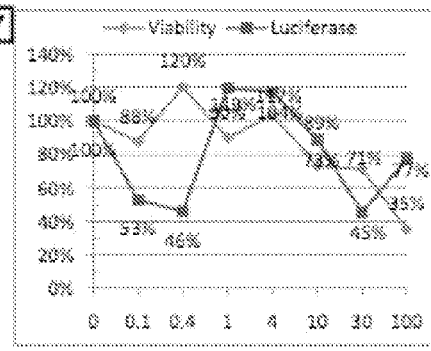
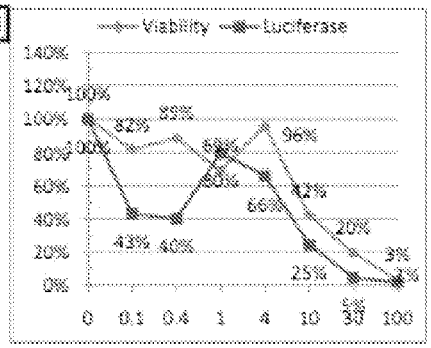
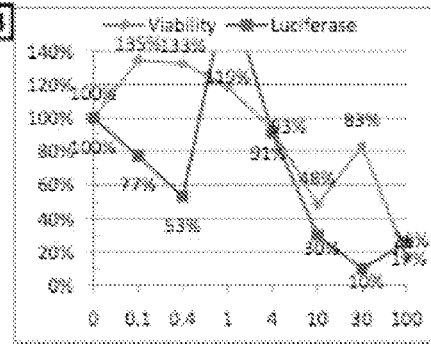
Figure 2 CON [3]

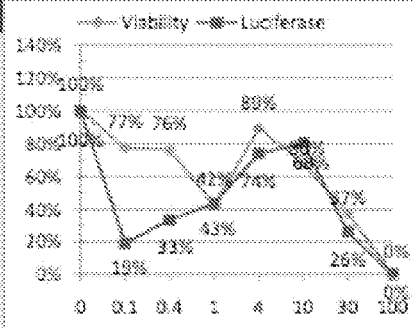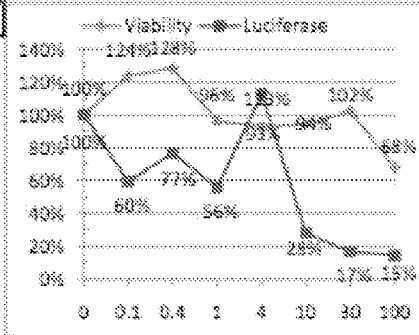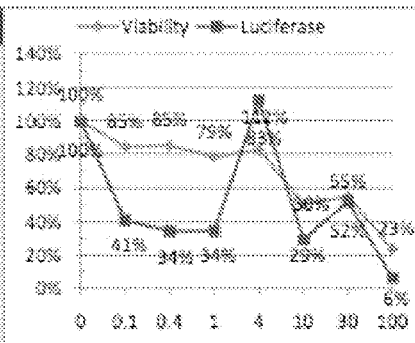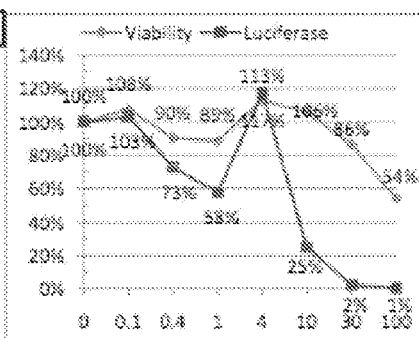
Figure 2 CON [4]

(Compound 13) $C_{21} H_{21} Cl N_6 O S$ (M.W.=441)
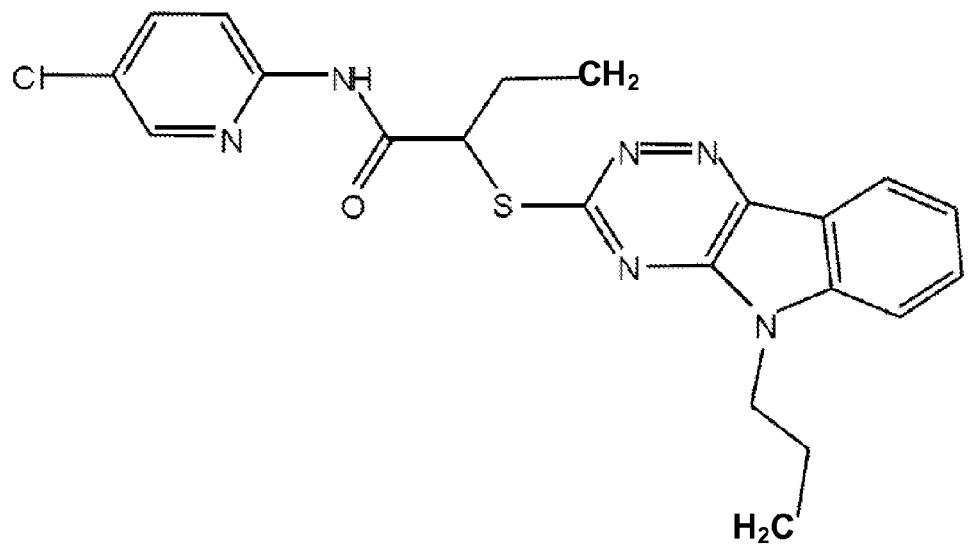
(Compound 14) $C_{37} H_{33} F N_2 O_2$ (M.W.=557)
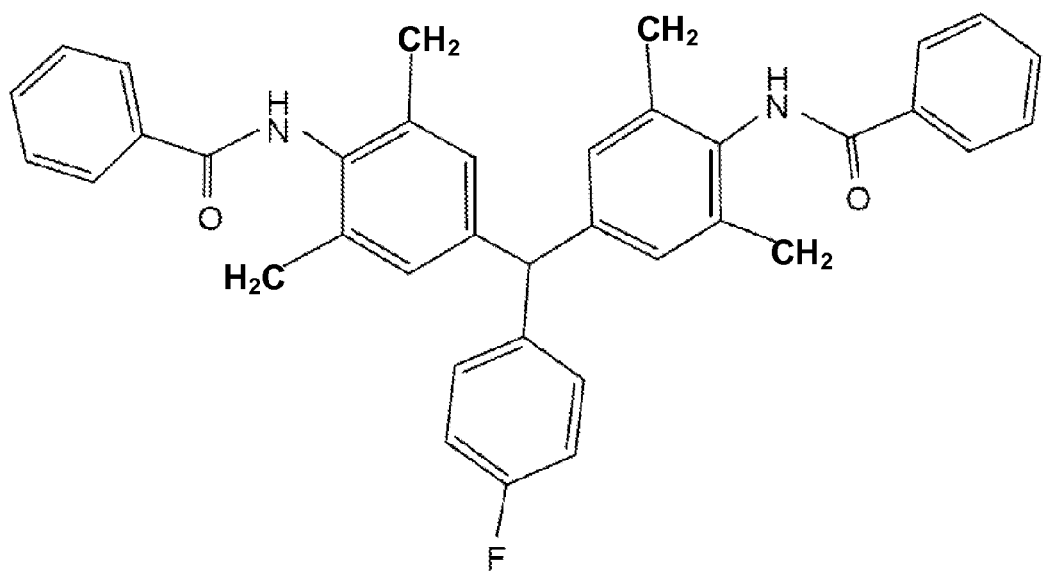
Figure 7

| 4 μM 13-analog Compounds | | Viability Assay | | Luciferase Assay | |
|---|---|---|---|---|---|
| CP well No. | ID | Mean | (%) | Mean | (%) |
| CP A03 | SMSF0042567 | 5177 | 3.01% | (661) | -8.01% |
| CP A05 | SMSF0042560 | 115598 | 67.11% | 5450 | 66.00% |
| CP A07 | SMSF0042537 | 228295 | 132.54% | 3920 | 47.47% |
| CP A09 | SMSF0042539 | 240459 | 139.60% | 5572 | 67.48% |
| CP A11 | SMSF0042540 | 225908 | 131.15% | 5400 | 65.40% |
| CP A13 | SMSF0042556 | 209402 | 121.57% | 6528 | 79.06% |
| CP A15 | SMSF0042541 | 239178 | 138.86% | 8551 | 103.56% |
| CP A17 | SMSF0042550 | 215109 | 124.88% | 9632 | 116.65% |
| CP A19 | SMSF0017943 | 115598 | 67.11% | (463) | -5.61% |
| CP A21 | SMSF0047024 | 185758 | 107.84% | 5280 | 63.94% |
| CP C03 | SMSF0047025 | 205936 | 119.56% | 5276 | 63.89% |
| CP C05 | SMSF0047375 | 208089 | 120.81% | 4822 | 58.40% |
| CP C07 | SMSF0047383 | 186313 | 108.17% | 4638 | 56.17% |
| CP C09 | SMSF0047376 | 152854 | 88.74% | 9868 | 119.51% |
| CP C11 | SMSF0047377 | 175473 | 101.87% | 8056 | 97.56% |
| CP C13 | SMSF0016237 | 165827 | 96.27% | 8702 | 105.39% |
| CP C15 | SMSF0050083 | 131804 | 76.52% | 24710 | 299.25% |
| CP C17 | SMSF0050139 | 237474 | 137.87% | 4588 | 55.56% |
| CP C19 | SMSF0051346 | 254725 | 147.88% | 7061 | 85.51% |
| CP C21 | SMSF0050615 | 272899 | 158.43% | 7256 | 87.87% |
| CP E03 | SMSF0050536 | 268161 | 155.68% | 6603 | 79.97% |
| CP E05 | SMSF0050601 | 296846 | 172.34% | 5980 | 72.42% |
| CP E07 | SMSF0050537 | 276932 | 160.77% | 6727 | 81.47% |
| CP E09 | SMSF0050618 | 228814 | 132.84% | 25446 | 308.16% |
| CP E11 | SMSF0050604 | 127205 | 73.85% | 13022 | 157.70% |
| CP E13 | SMSF0052091 | 234625 | 136.21% | 7298 | 88.38% |
| CP E15 | SMSF0052089 | 236800 | 137.48% | 5405 | 65.46% |
| CP E17 | SMSF0053732 | 255450 | 148.30% | 4671 | 56.57% |
| CP E19 | SMSF0052670 | 253200 | 147.00% | 3945 | 47.78% |
| 1 % DMSO | N/A | 172249 | 100.00% | 8257 | 100.00% |

Figure 8

| 14 and 14-analog Compounds: Dose-Dependent Assays | | | |
|---|---|---|---|
| ID (No.) | Chembridge No. | Viability IC$_{50}$ (µM) | Infectivity IC$_{50}$ (µM) |
| 14 | 5367380 | > 100 | 0.4 ~ 1 |
| 14-1 | 5102771 | 30 ~ 100 | 30 ~ 100 |
| 14-2 | 5116635 | > 100 | > 100 |
| 14-3 | 5363579 | > 100 | ~ 100 |
| 14-4 | 5363585 | 30 ~ 100 | 30 ~100 |
| 14-5 | 5366125 | > 100 | ~ 30 |
| 14-6 | 5557820 | > 100 | > 100 |
| 14-7 | 6512962 | > 100 | 0 ~ 0.1 |
| 14-8 | 5102767 | 30 ~ 100 | 30 ~ 100 |
| 14-9 | 5180300 | > 100 | > 100 |
| 14-10 | 5181140 | > 100 | > 100 |
| 14-11 | 5180568 | 30 ~ 100 | 10 ~ 30 |
| 14-12 | 5358649 | > 100 | > 100 |
| 14-13 | 5471764 | > 100 | > 100 |
| 14-14 | 7298931 | > 100 | > 100 |
| 14-15 | 7304675 | > 100 | > 100 |

Figure 9

DRUGS TO TREAT HPV INFECTION

CROSS-REFERENCE TO RELATED APPLICATIONS

This application claims priority to PCT International Application No. PCT/US2009/045680 filed on May 29, 2009, which claims priority to U.S. provisional application Ser. No. 61/130,270 filed May 29, 2008, both of which is are incorporated by reference in its their entirety for all purposes.

STATEMENT REGARDING FEDERALLY SPONSORED RESEARCH OR DEVELOPMENT

This invention was made with government support under AI071947 awarded by the National Institutes of Health. The government has certain rights in the invention.

BACKGROUND OF THE INVENTION

Human papillomaviruses (HPV) are small, non-enveloped, double-stranded DNA viruses that infect the cutaneous and/or mucosal epithelium. Over 100 HPV genotypes are known to exist. A subset of HPVs that are mucosotropic, infecting the anogenital tract of men and women, are the most common sexually transmitted human pathogens. These sexually transmitted, mucosotropic HPVs are further subcategorized as high risk (e.g. HPV16 and HPV18) or low risk (HPV6 and HPV11) depending on their oncogenicity. High risk genotypes are causally associated with anogenital cancers including nearly 100% of cervical carcinomas, the second leading cause of death from cancer in women worldwide.

While an effective prophylactic vaccine against two of the most common high risk HPVs is now available, the high cost, issues with social acceptance, and limitations in health care systems through which the vaccine can be provided will likely limit the availability of this vaccine to women particularly in developing countries where HPV-associated anogenital cancers are most commonly found. Consequently there remains a need to identify other, less expensive and more universally available approaches for preventing sexually transmitted HPV infections. HPV microbicides that can be added to vaginal lubricants, condom lubricants, and spermicidal creams would provide one such route of control. The disclosure of this application identifies such microbicides.

There is a tight link between the differentiation program of the natural host cells, keratinocytes, and the HPV life cycle. Consequently it has been difficult to produce mature infectious HPV particles at a large scale and this has greatly restricted studies to identify HPV microbicides. We have recently developed transfection methods that generate large yields of virus particles, and efficient encapsidation of target plasmids as large as the full length ~8 kb HPV genome have overcome this limitation. These techniques provide a genetically modifiable, high yield source of infectious HPV and HPV pseudoviruses expressing reporter genes for studies designed to identify HPV microbicides. U.S. Ser. No. 11/275,819, Production of Packaged DNA Sequences—Paul G. Ahlquist, et al., filed Jan. 30, 2006, discloses this novel assay system and is incorporated by reference herein.

Needed in the art is an affordable, universally available approach for preventing sexually transmitted HPV infections.

SUMMARY OF INVENTION

The present invention is a method of inhibiting papillomavirus infection.

In a first aspect, the present invention is a method of inhibiting papillomavirus infection, comprising the step of exposing tissues or cells that are susceptible to papillomavirus infection to an effective amount of a compound of the formula (I):

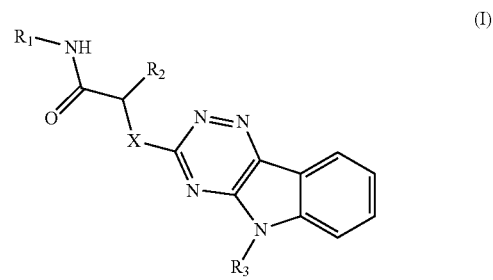

(I)

wherein $R_1$ is an aryl group, a substituted aryl group, a heteroaryl group, or a substituted heteroaryl group, $R_2$ is a straight chain or branched alkyl group consisting of 1-5 carbon atoms, $R_3$ is a straight chain or branched alkyl group consisting of 1-5 carbon atoms, and X is an oxygen or a sulfur atom.

In one embodiment of the first aspect, the substituted heteroaryl group is selected from the group consisting of a mono-substituted heteroaryl group and a di-substituted heteroaryl group.

In a second aspect, the present invention is a method of inhibiting papillomavirus infection, comprising the step of exposing tissues or cells that are susceptible to papillomavirus infection to an effective amount of a compound of the formula (II):

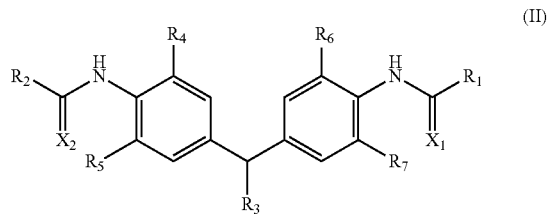

(II)

wherein $R_1$ is a straight chain or branched alkyl group consisting of 1-5 carbon atoms, an aryl group, or a substituted aryl group, $R_2$ is a straight chain or branched alkyl consisting of 1-5 carbon atoms, an aryl group, or a substituted aryl group, $R_3$ is an aryl group or a substituted aryl group, $R_4$ is H, $CH_3$, $CH_2CH_3$, or a halogen, $R_5$ is H, $CH_3$, $CH_2CH_3$, or a halogen, $R_6$ is H, $CH_3$, $CH_2CH_3$, or a halogen, $R_7$ is H, $CH_3$, $CH_2CH_3$, or a halogen, $X_1$ is an oxygen or a sulfur atom, and $X_2$ is an oxygen or a sulfur atom.

In a third aspect, the present invention is a method of inhibiting papillomavirus infection, comprising the step of exposing tissues or cells that are susceptible to papillomavirus infection to an effective amount of a compound of the formula (III):

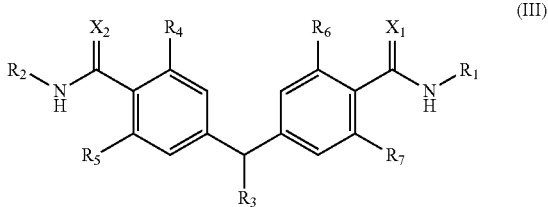

wherein $R_1$ is a straight chain or branched alkyl group consisting of 1-5 carbon atoms, an aryl group, or a substituted aryl group, $R_2$ is a straight chain or branched alkyl group consisting of 1-5 carbon atoms, an aryl group, or a substituted aryl group, $R_3$ is an aryl group, or a substituted aryl group, $R_4$ is H, $CH_3$, $CH_2CH_3$, or a halogen, $R_5$ is H, $CH_3$, $CH_2CH_3$, or a halogen, $R_6$ is H, $CH_3$, $CH_2CH_3$, or a halogen, $R_7$ is H, $CH_3$, $CH_2CH_3$, or a halogen, $X_1$ is an oxygen or a sulfur atom, and $X_2$ is an oxygen or a sulfur atom.

In a fourth aspect, the present invention is a method of inhibiting papillomavirus infection, comprising the step of exposing tissues or cells that are susceptible to papillomavirus infection to an effective amount of a compound of the formula (IV):

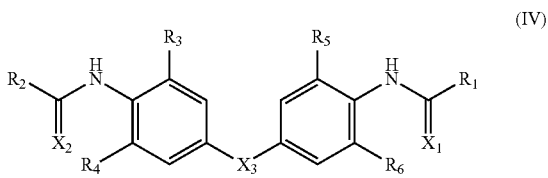

wherein $R_1$ is a straight chain or branched alkyl group consisting of 1-5 carbon atoms, an aryl group, or a substituted aryl group, $R_2$ is a straight chain or branched alkyl group consisting of 1-5 carbon atoms, an aryl group, or a substituted aryl group, $R_3$ is H, $CH_3$, $CH_2CH_3$, or a halogen, $R_4$ is H, $CH_3$, $CH_2CH_3$, or a halogen, $R_5$ is H, $CH_3$, $CH_2CH_3$, or a halogen, $R_6$ is H, $CH_3$, $CH_2CH_3$, or a halogen, $X_1$ is an oxygen or a sulfur atom, $X_2$ is an oxygen or a sulfur atom, and $X_3$ is an oxygen atom, a sulfur atom, or an NH group.

In a fifth aspect, the present invention is a method of inhibiting papillomavirus infection, comprising the step of exposing tissues or cells that are susceptible to papillomavirus infection to an effective amount of a compound of the formula (V):

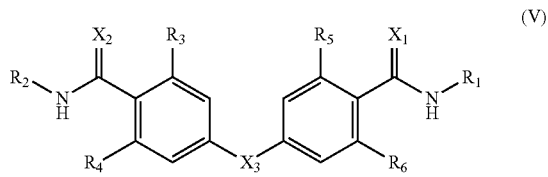

wherein $R_1$ is a straight chain or branched alkyl group consisting of 1-5 carbon atoms, an aryl group, or a substituted aryl group, $R_2$ is a straight chain or branched alkyl group consisting of 1-5 carbon atoms, an aryl group, or a substituted aryl group, $R_3$ is H, $CH_3$, $CH_2CH_3$, or a halogen, $R_4$ is H, $CH_3$, $CH_2CH_3$, or a halogen, $R_5$ is H, $CH_3$, $CH_2CH_3$, or a halogen, $R_6$ is H, $CH_3$, $CH_2CH_3$, or a halogen, $X_1$ is an oxygen or a sulfur atom, $X_2$ is an oxygen or a sulfur atom, and $X_3$ is an oxygen atom, a sulfur atom, or an NH group.

In one embodiment of the first through fifth aspects, the substituted aryl group is selected from the group consisting of a mono-substituted aryl group and a di-substituted aryl group.

In one embodiment of the second through fifth aspects, the halogen is selected from the group consisting of F, Cl, and Br.

In a sixth aspect, the present invention is a method of inhibiting papillomavirus infection, comprising the step of exposing tissues or cells that are susceptible to papillomavirus virus infection to an effective amount of a compound selected from the group consisting of Compound 13, Compound 14, formula (I), formula (II), formula (III), formula (IV), formula (V), and mixtures thereof:

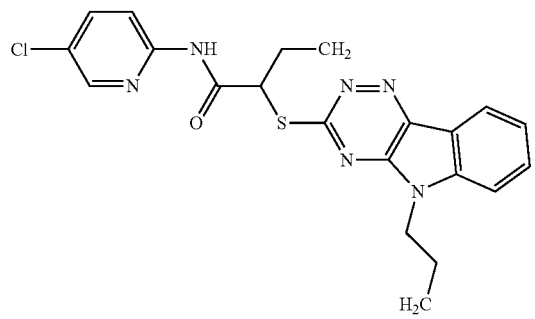

(Compound 13)

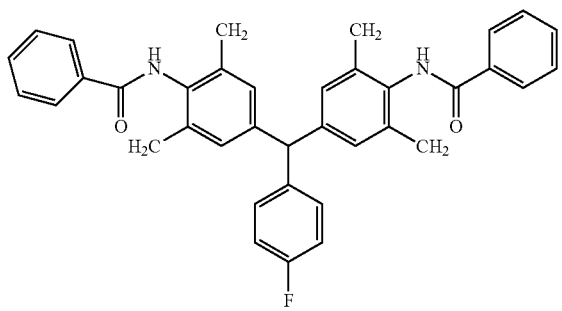

(Compound 14)

In one embodiment of the first through sixth aspects, the papillomavirus is HPV. In different embodiments of the first through sixth aspects, the HPV is high risk HPV or low risk HPV. In further embodiments of the first through sixth aspects, the tissue or cells are selected from the group consisting of vulvovaginal tissues and cells, rectal tissue and cells, oral cavity tissue and cells, and oral pharynx tissue and cells. In another embodiment of the first through sixth aspects, an effective amount of a compound selected from the group consisting of Compound 13, Compound 14, formula (I), formula (II), formula (III), formula (IV), formula (V), and mixtures thereof is in the range of preferably 0.1 uM to 100 mM, more preferably 1 mM to 10 mM.

In a seventh aspect, the present invention is a composition comprising an effective amount of a compound selected from the group consisting of Compound 13, Compound 14, formula (I), formula (II), formula (III), formula (IV), formula (V), and mixtures thereof and a pharmaceutically acceptable carrier, wherein the compound is effective for inhibiting papillomavirus infection.

In an eight aspect, the present invention is a composition comprising an effective amount of a compound selected from the group consisting of Compound 13, Compound 14, formula (I), formula (II), formula (III), formula (IV), formula (V), and mixtures thereof and a product designed for application in the vaginal or rectal areas. In one embodiment of the eighth aspect, the product designed for application in the vaginal or rectal areas is a spermicide, lubricant, cream, ointment, solution, powder, impregnated tampon, rectal or vaginal suppository, pessary, or implant.

In a ninth aspect, the present invention is a composition comprising an effective amount of a compound selected from the group consisting of Compound 13, Compound 14, formula (I), formula (II), formula (III), formula (IV), formula (V), and mixtures thereof and a product designed for application by inhalation into the respiratory system. In one embodiment of the ninth aspect, the product designed for application by inhalation into the respiratory system is a spray, aerosol, or foam.

BRIEF DESCRIPTION OF THE DRAWINGS

FIG. 6A is a mock infection negative control. Nuclei are stained. Note perinuclear localization of HPV16 particles in the absence or presence of inhibitory compound, demonstrating that the step at which the compounds inhibit infection must be post entry.

FIG. 7. Structures of the two lead compounds Compound 13 (N-(5-chloro-2-pyridinyl)-2-[(5-propyl-5H-[1,2,4]tri-azino[5,6-b]indol-3-yl)thio]butanamide) and Compound 14 (N,N'-[[(4-fluorophenyl)methylene]bis(2,6-dimethyl-4,1-phenylene)]dibenzamide).

FIG. 8. Analysis of analogs of Compound 13. Shown are the viability and infectivity (Luciferase reporter) assays in HaCaT for drugs similar in structure to compound 13. All drugs were tested at 4 uM.

FIG. 9. Analysis of analogs of Compound 14. Shown are Viability and Infectivity IC50s for analogs, and parent compound 14 based upon infectivity assays in HaCaT cells exposed to 0.01 to 100 uM of drug. Assays were performed as described in FIG. 2.

DETAILED DESCRIPTION OF THE INVENTION

A. In General

Anogenital HPVs are the most common sexually transmitted pathogens and the chief cause of anogenital cancers including cervical, vaginal, vulvar, penile, and anal cancers. Recently developed vaccines may provide some level of protection against a subset of these viruses, however, their use is still limited due to cost, social acceptance, and access to health care providers. The goal was to identify novel, small molecule microbicides to prevent infections by sexually transmitted human papillomaviruses.

To identify HPV microbicides, we used HPV pseudoviruses encapsidating a reporter gene described in U.S. Ser. No. 11/275,819 to screen over 40,000 small molecules for ones that inhibit early events in the HPV infectious life cycle. From this screen we identified a subset of compounds that efficiently blocked HPV infection.

Importantly, two of these compounds appear to work at steps post-entry. Entry process for HPVs is slow, in the range of many hours, which means the microbicides may be effective, not only when used at the time of exposure to HPV, but also within a defined period post-exposure.

B. Compounds

Using a high throughput screen (HTS) of over 40,000 small molecules, we identified potent lead compounds that are highly effective at inhibiting early steps in HPV infection. These compounds have $IC_{50}$'s in the sub-micromolar range and little to no toxicity. The HTS monitored in 293T cells the infectivity of HPV16 pseudoviruses, which have encapsidated in them the plasmid, pSEAP, directing expression of the secreted alkaline phosphatase (SEAP) reporter gene from the SV40 early promoter. Alkaline phosphatase activity and cell viability were assayed in parallel allowing identification of drugs that specifically inhibit early steps of HPV infection (i.e. binding, entry, delivery of encapsidated DNA to the nucleus and expression of encapsidated genes) without altering cellular viability (i.e. metabolic activity). The HTS is explained in detail in Example 1.

Figure 2:
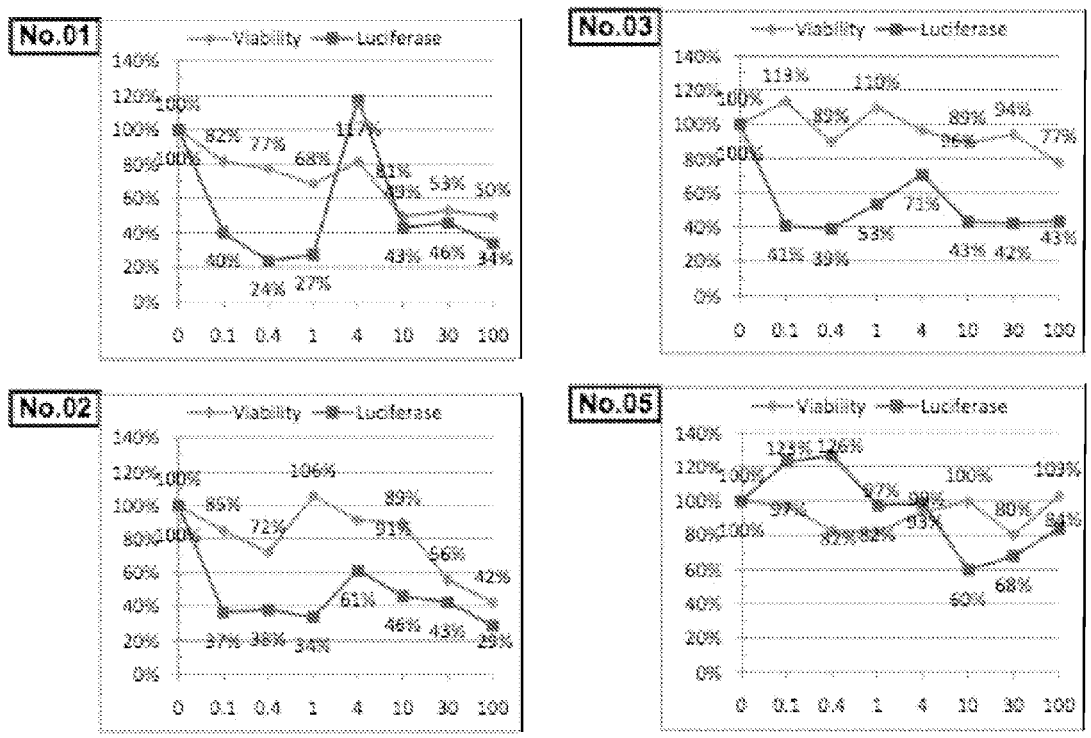
FIG. 2. Dose dependence inhibition of HPV16 pseudovirus infection in a human keratinocyte cell line (HaCaT). Graphed are the dose-dependent effects of lead compounds shown in Table 2 on the efficiency of infection by HPV16 pseudovirus scored by measuring luciferase reporter activity (squares) as well as their effects on cell viability (circles). Not included here are the dose curves for two compounds, 4 (assayed independently and found to inhibit infection but also to cause cytotoxicity at similar doses) and 6 (no longer commercially available). Note: the data for the 4 µM concentration of many drugs may be anomalous as the % infection does not correlate with lower concentrations, leading us to believe there was some error in this dilution.
Figure 3:
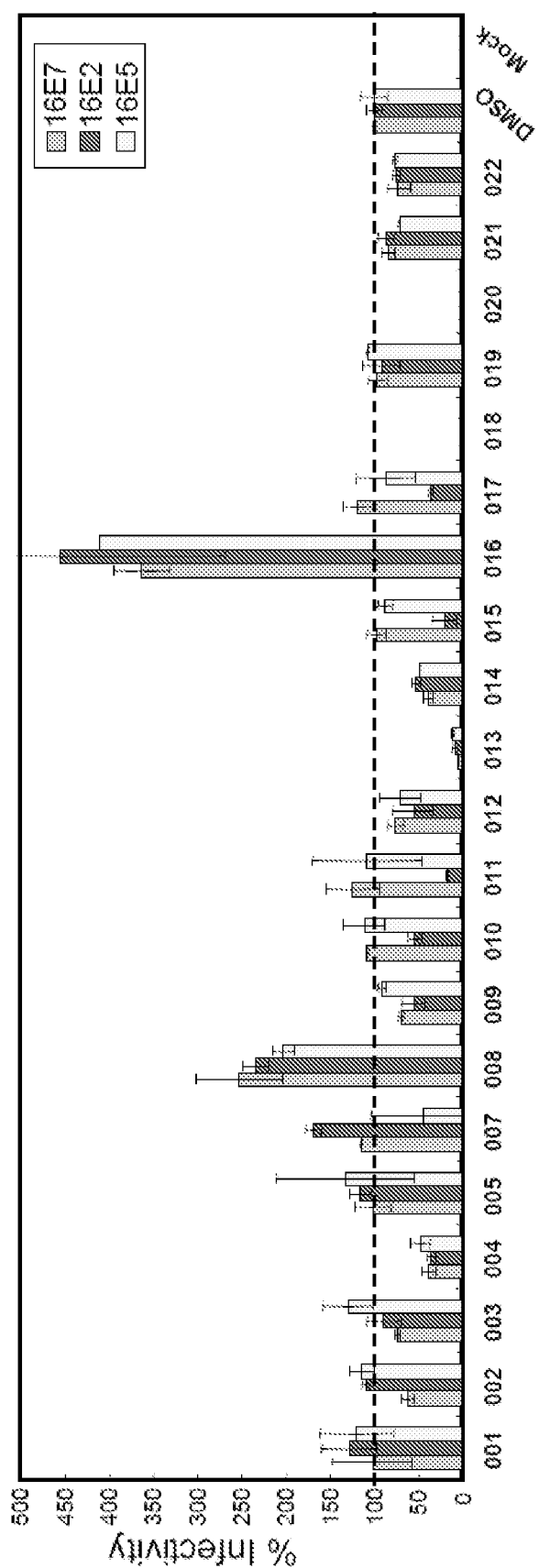
FIG. 3. Inhibition of infection by HPV 16 virus. Shown is the relative efficiency of infection by HPV16 virus in 293T cells as scored by quantifying early viral transcription using real time PCR for E2 (dark grey bars), E5 (white bars) and E7 (light grey bars) containing mRNAs at 48 hours post-infection in the absence (DMSO—vehicle only, values set at 100%) or the presence of the indicated compound (10 uM concentration). Data points shown are the average of triplicate sample values. The dotted line indicates the normalized value for no drug (set as 100% infection value). Note Compounds 4, 13, 14, 18, and 20 all indicated reproducible and significant inhibition of HPV16 early gene expression.
Figure 4:
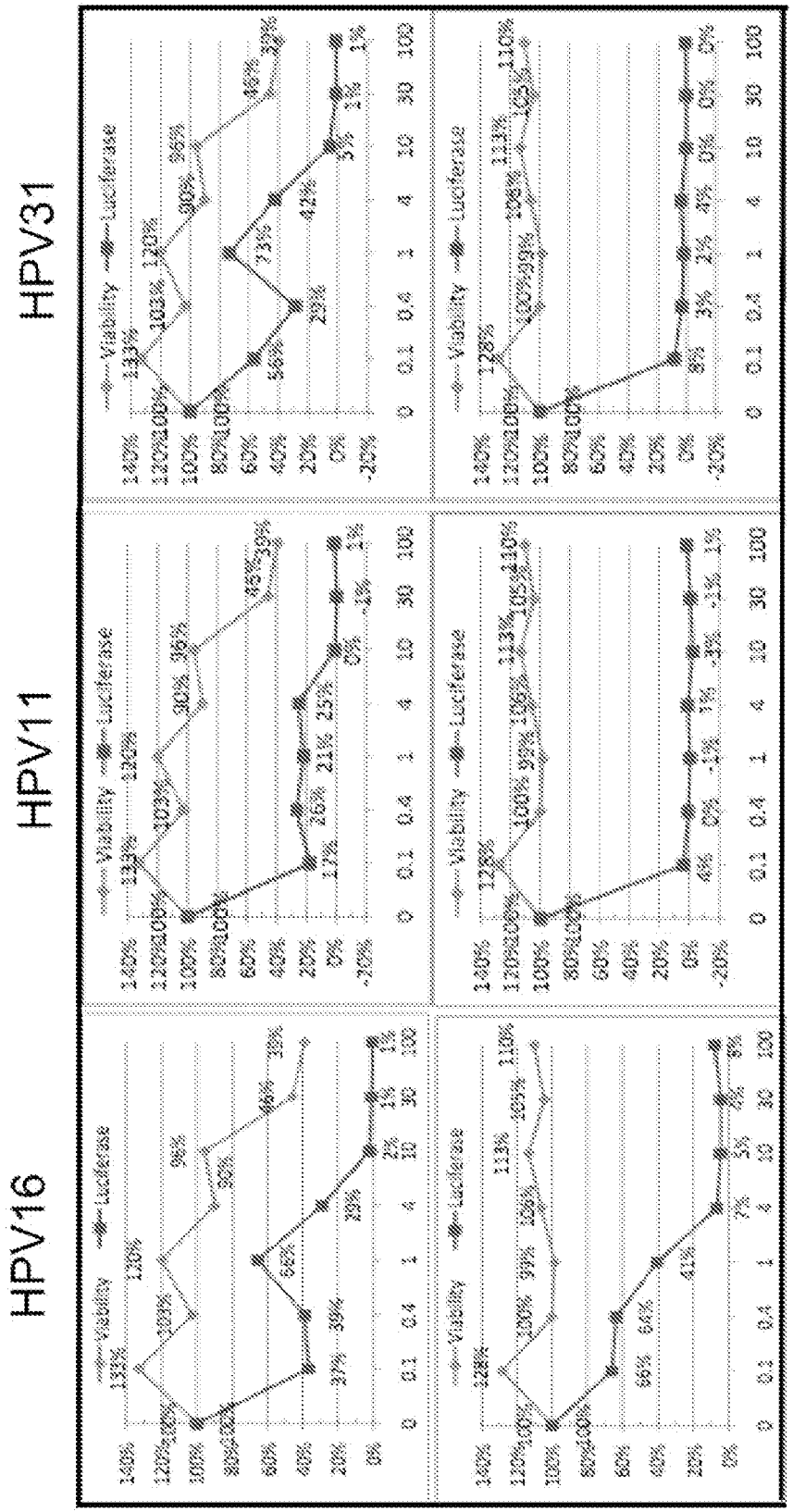
FIG. 4. Compounds 13 and 14 can inhibit infection by multiple anogenital HPVs. Shown are results from infection experiments in HaCaT cells monitoring the efficiency of infection by HPV16, HPV11 and HPV31 pseudovirus carrying the firefly luciferase gene in the absence (0 uM, vehicle only) or increasing concentrations (0.1 to 100 uM) of Compound 13 or 14. The Y axis is the relative efficiency of infection (squares) or cell viability (circles) as a function of drug concentration (X axis). All data points represent the average of values from triplicate samples. Note that both Compounds 13 and 14 displayed submicromolar $IC_{50}$s for all three HPV pseudovirus infections. Data for HPV16 is the also plotted in FIG. 2.
Figure 5:
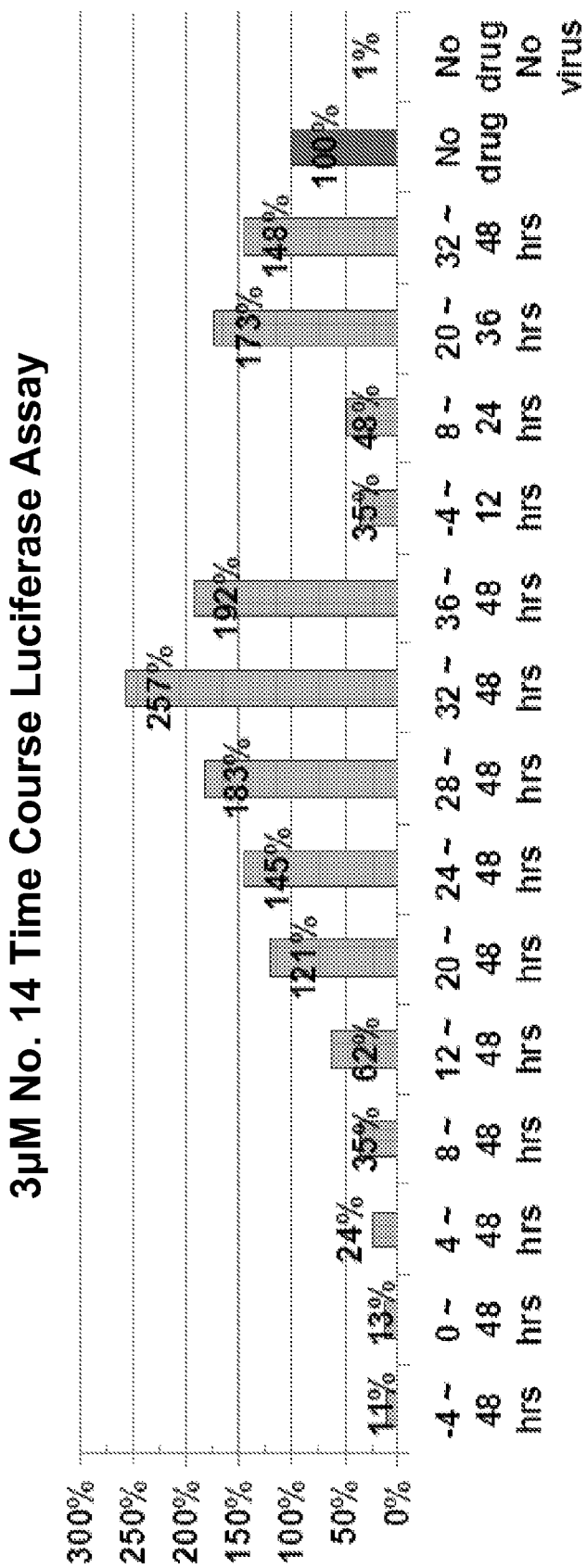
FIG. 5. Level of infection by HPV16 pseudovirus carrying luciferase reporter gene exposed to HaCaT cells that were not exposed to any microbicide (labeled No drug) or exposed to compound 14 (3 uM) for indicated time periods with reference to the time of exposure to pseudovirus. First bar reflects continuous exposure to drug throughout the experiment as is akin to what was done in prior experiments (FIGS. 1-4).

Lead compounds were subjected to secondary screens including screens with bonafide HPV16 particles (FIG. 2) and HPV pseudoviruses of other HPV genotypes (FIG. 3). Dose response curves were also performed to establish $IC_{50}$'s and to assess cytotoxicity (FIG. 4). Because we had previously determined that drugs inhibiting the cell cycle could inhibit infectivity we also determined whether the newly identified drugs were cell cycle inhibitors. They were not (data not shown).

Two compounds, Compound 13 and Compound 14 (see FIG. 7), were selected from these studies for additional analyses based upon their having low (submicromolar $IC_{50}$'s, little to no cytotoxicity, and effectiveness in inhibiting multiple HPV genotypes. These additional studies demonstrate the capacity of the two selected compounds to inhibit HPV infection optimally when cells are exposed to the drugs between 4 and 12 hours of exposure to the virus, the time period when exposure to the vehicles (vaginal/penile lubricants, contraceptive jellies) would be expected. Drugs similar to Compounds 13 and 14 were screened to identify the essential pharmacophore structures and modifications that effect activity.

In one embodiment, the present invention is a method of inhibiting HPV virus infection in human or non-human animals. In its broadest form, the method involves exposing a papovavirus to an effective amount of a compound selected from the group consisting of Compound 13, Compound 14, and their analogs.

By "Compound 13" and "Compound 14", or any other compound disclosed in this application, we mean a suitable compound disclosed within the present application and pharmaceutically acceptable salts, solvates, and isomers thereof. The compound may also be combined with a pharmaceutically acceptable carrier or diluent.

By "effective amount" we mean an amount effective to inhibit HPV infection preferably 95%, more preferably 99%, and most preferably 100%.

Compounds 13 and 14 are available commercially from ChemBridge Corporation.

In one embodiment of the present invention the method involves exposing a papovavirus to an effective amount of an analog of Compound 13. A preferable analog of Compound 13 is a compound having the formula (I):

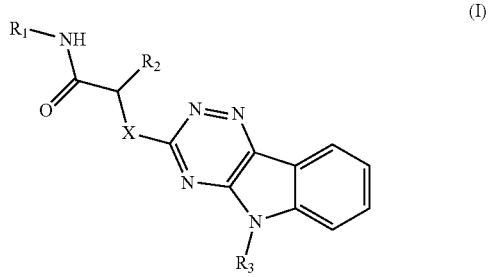

wherein $R_1$ is an aryl group, a mono-substituted aryl group, a di-substituted aryl group, a heteroaryl group, a mono-substituted heteroaryl group, or a di-substituted heteroaryl group, $R_2$ is a straight chain or branched alkyl group consisting of 1-5 carbon atoms, $R_3$ is a straight chain or branched alkyl group consisting of 1-5 carbon atoms, and X is an oxygen or a sulfur atom.

In another embodiment, the method involves exposing a papovavirus to an effective amount of an analog of Compound 14. A preferable analog is a compound having the formula (II), (III), (IV), or (V):

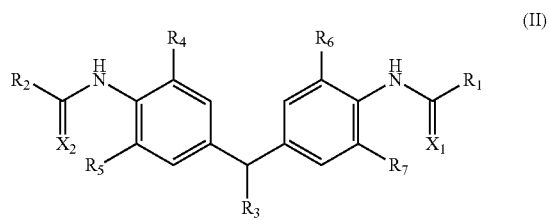

wherein $R_1$ is a straight chain or branched alkyl group consisting of 1-5 carbon atoms, an aryl group, a mono-substituted aryl group, or a di-substituted aryl group, $R_2$ is a straight chain or branched alkyl consisting of 1-5 carbon atoms, an aryl group, a mono-substituted aryl group, or a di-substituted aryl group, $R_3$ is an aryl group, a mono-substituted aryl group, or a di-substituted aryl group, $R_4$ is H, $CH_3$, $CH_2CH_3$, F, Cl, or Br, $R_5$ is H, $CH_3$, $CH_2CH_3$, F, Cl, or Br, $R_6$ is H, $CH_3$, $CH_2CH_3$, F, Cl, or Br, $R_7$ is H, $CH_3$, $CH_2CH_3$, F, Cl, or Br, $X_1$ is an oxygen or a sulfur atom, and $X_2$ is an oxygen or a sulfur atom;

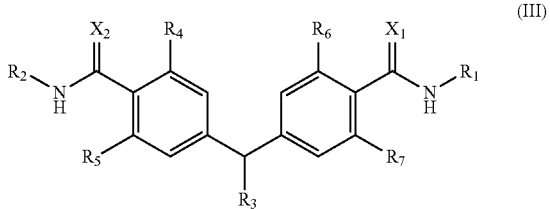

wherein $R_1$ is a straight chain or branched alkyl group consisting of 1-5 carbon atoms, an aryl group, a mono-substituted aryl group, or a di-substituted aryl group, $R_2$ is a straight chain or branched alkyl group consisting of 1-5 carbon atoms, an aryl group, a mono-substituted aryl group, or a di-substituted aryl group, $R_3$ is an aryl group, a mono-substituted aryl group, or a di-substituted aryl group, $R_4$ is H, $CH_3$, $CH_2CH_3$, F, Cl, or Br, $R_5$ is H, $CH_3$, $CH_2CH_3$, F, Cl, or Br, $R_6$ is H, $CH_3$, $CH_2CH_3$, F, Cl, or Br, $R_7$ is H, $CH_3$, $CH_2CH_3$, F, Cl, or Br, $X_1$ is an oxygen or a sulfur atom, and $X_2$ is an oxygen or a sulfur atom;

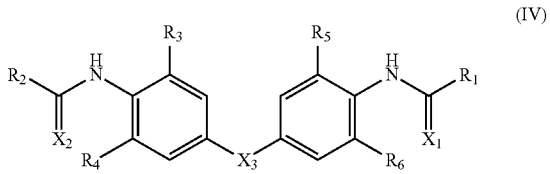

wherein $R_1$ is a straight chain or branched alkyl group consisting of 1-5 carbon atoms, an aryl group, a mono-substituted aryl group, or a di-substituted aryl group, $R_2$ is a straight chain or branched alkyl group consisting of 1-5 carbon atoms, an aryl group, a mono-substituted aryl group, or a di-substituted aryl group, $R_3$ is H, $CH_3$, $CH_2CH_3$, F, Cl, or Br, $R_4$ is H, $CH_3$, $CH_2CH_3$, F, Cl, or Br, $R_5$ is H, $CH_3$, $CH_2CH_3$, F, Cl, or Br, $R_6$ is H, $CH_3$, $CH_2CH_3$, F, Cl, or Br, $X_1$ is an oxygen or a sulfur atom, and $X_2$ is an oxygen or a sulfur atom, and $X_3$ is an oxygen atom, a sulfur atom, or an NH group; or (V)

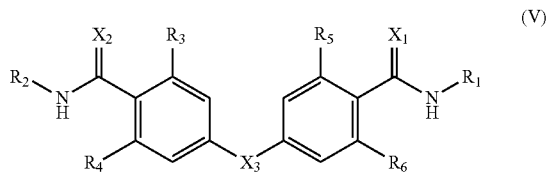

wherein $R_1$ is a straight chain or branched alkyl group consisting of 1-5 carbon atoms, an aryl group, a mono-substituted aryl group, or a di-substituted aryl group, $R_2$ is a straight chain or branched alkyl group consisting of 1-5 carbon atoms, an aryl group, a mono-substituted aryl group, or a di-substituted aryl group, $R_3$ is H, $CH_3$, $CH_2CH_3$, F, Cl, or Br, $R_4$ is H, $CH_3$, $CH_2CH_3$, F, Cl, or Br, $R_5$ is H, $CH_3$, $CH_2CH_3$, F, Cl, or Br, $R_6$ is H, $CH_3$, $CH_2CH_3$, F, Cl, or Br, $X_1$ is an oxygen or a sulfur atom, and $X_2$ is an oxygen or a sulfur atom, and $X_3$ is an oxygen atom, a sulfur atom, or an NH group.

Analogs of Compounds 13 and 14 are available commercially from ChemBridge Corporation.

C. Inhibited Viruses

In one broad embodiment, the present invention is a method and composition for inhibition of papovaviruses, such as human papillomaviruses (HPVs). In one version of the present invention, the method would be used to inhibit all HPVs. In another embodiment, the invention would be used to inhibit high risk HPVs, such as HPV16, 18, 31, 33, 35, 39, 45, 51, 52, 56, 58, 59, 66, and 68. In a further embodiment, the invention would be used to inhibit low risk HPVs, such as HPV6 and HPV11. In a specific embodiment, the invention is used to inhibit HPV16, HPV31 and HPV11.

D. Tissues and Cells

In one embodiment, the present invention is a method of blocking the establishment of viral infection by blocking at a point post-entry and interfering with early viral gene expression. Preferably, the virus is either HPV16 or one of the viruses discussed above. In a preferred embodiment of the present invention, one would apply the inhibitor to body surfaces susceptible to viral infection.

In one embodiment of the present invention, one would administer an inhibitor selected from the group consisting of Compound 13 and Compound 14 and their analogs to a susceptible tissue or cell (FIG. 7-9). By "susceptible tissue or cell", we mean a tissue or cell that is capable of infection by papillomavirus, preferably HPV. So far, the only confirmed method of HPV transmission is by direct and indirect personal contact, including sexual activities. Preferred tissues and cells would include the vulvovaginal and rectal tissues. However, as HPV also infects mouth and throat tissue, HPV transmission might be much more complicated than we know now. Additional preferred tissues would be those of the oral cavity and oral pharynx.

E. Treatment Methods

In one embodiment, if one wished to prevent HPV infection, one would add the compound to a spermicide, lubricants, or other product designed for application in the vaginal area. In another preferred embodiment, the pharmaceutical composition may be selected from the group consisting of rectal or vaginal suppositories, ointments, solutions, powders, and impregnated tampons. In another embodiment of the present invention, the pharmaceutical composition is administered as a spray, aerosol or foam.

Vaginal or vulvovaginal delivery of a medication may be by a device, such as disclosed in U.S. Ser. Nos. 11/763,085 and 11/454,604. A "vulvovaginal surface" herein denotes any external or internal surface of the female genitalia, including mucosal surfaces in the vaginal cavity and nonmucosal surfaces of the vulva and immediately surrounding areas of skin. In some embodiments, the composition is more specifically adapted for application to a vaginal mucosal surface, and an external phase of the composition is bioadhesive to such a surface.

A composition used in methods of the invention can be in any suitable form that is adapted for vulvovaginal administration. For intravaginal administration, suitable forms include a vaginal cream, tablet, suppository, pessary, or implant, but in particular embodiments, the composition is in the form of a vaginal cream.

The composition can be administered topically to external surfaces of skin surface, preferably the vulva and/or to surrounding areas of skin. In addition or alternatively, the composition can be administered intravaginally. In one embodiment, the composition is a vaginal cream, i.e., a semi-solid formulation adapted for administration to vaginal mucosal surfaces.

A vaginal cream for use according to methods of the invention can be administered to contact a mucosal surface in the vaginal cavity by means, for example, of an applicator that is optionally pre-filled with a single unit dosage amount of the cream. With the patient optionally in a supine position, the tip of the applicator can be gently inserted high in the vagina, for example in the posterior vaginal formix, and the cream can be released through the tip by pushing on a plunger of the applicator.

In some embodiments anal or rectal delivery of the inhibitor would be preferred. Suitable formulations for rectal administration include, for example, suppositories, which consist of the inhibitor with a suppository base. Suitable suppository bases include natural or synthetic triglycerides or paraffin hydrocarbons. In addition, it is also possible to use gelatin rectal capsules which consist of a combination of the packaged inhibitor with a base, including, for example, liquid triglycerides, polyethylene glycols, and paraffin hydrocarbons. Another option is the use of penile lubricants.

F. Dose and Concentration

Infection experiments in human keratinocyte cell line, HaCaT, monitoring the efficiency of infection by HPV16, HPV11, and HPV31 pseudovirus carrying the firefly luciferase gene were conducted in the absence or increasing concentrations (0.1 to 100 µM) of Compounds 13 and 14 (see FIG. 4). Submicromolar $IC_{50}$'s were demonstrated for all genotypes tested.

In vitro data were collected at 3 µM concentration. However, further analysis showed that 10 µM of Compound 13 and 4 µM of Compound 14 completely inhibited all the tested genotypes. A human treatment dosage is preferably between 0.1 µM and 100 mM, more preferably between 1 and 10 mM.

EXAMPLE I

Figure 1:
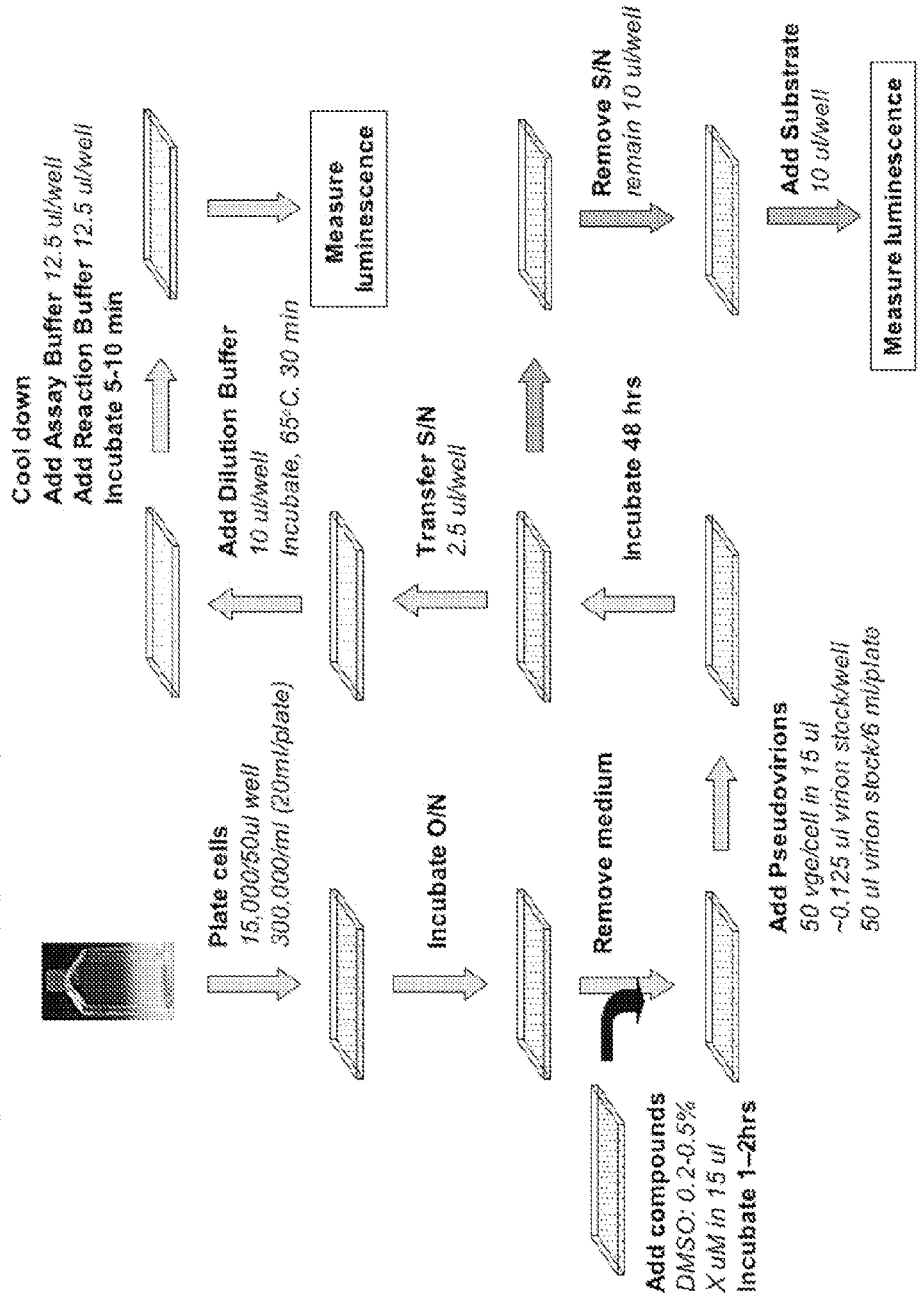
FIG. 1. High throughout screen (HTS) for identifying inhibitors of HPV infection. Shown is a schematic showing basic steps in the HTS. See also Example I, Materials and Methods, for additional details. Briefly, HPV16 pseudoviruses containing the SEAP reporter genes are analyzed for their ability to infect as judged by the levels of secreted alkaline phosphatase in the tissue culture supernatant (light grey arrows). Cell viability was assessed in parallel on the same wells (dark grey arrows). In the specific HTS carried out in this study, the compounds were added at 3 uM/1% DMSO final concentration (black arrow) 4 hours prior to infection.

Design, testing and use of a robust HTS for HPV infection. A facile, high throughput screen was designed to identify small molecules that inhibit early steps in HPV infection (FIG. 1). Briefly, the assay monitors in 293T cells the infectivity of HPV16 pseudoviruses, which have encapsidated in them the plasmid, pSEAP, directing expression of the secreted alkaline phosphatase (SEAP) reporter gene from the SV40 early promoter. Alkaline phosphatase activity and cell viability are assayed in parallel allowing one to identify drugs that specifically inhibit early steps in HPV infection (i.e. binding, entry, delivery of encapsidated DNA to the nucleus and expression of encapsidated genes) without altering cellular viability (i.e. metabolic activity).

To determine the robustness of this HTS, we initially screened a subset of compounds sourced from the Prestwick Chemical Library using a 384 well screening format. A total of 960 molecules were screened along with controls (neutralizing antibody and antiviral peptide EBx). Acceptable Z scores (range: 0.52 to 0.68) were obtained for the individual plates.

Given the robustness of the assay, we carried out a HTS of over 40,000 small molecules including 16,000 compounds from ChemBridge DIVERSet collection, 14,400 compounds from the Maybridge HitFinder library, 5,000 known bioactive compounds from NIH and from the Prestwick Chemical Library, and a number of compounds from smaller libraries available at the UW/Keck small molecule screening facility. The bioactive compound library screen led to the identification of a subset of cell cycle inhibitors that could inhibit HPV16 pseudovirus infection.

Follow-up studies on these lead bioactive compounds led to the demonstration that cell cycle progression is essential for early steps in HPV infection. From the HTS of all other libraries, 104 compounds of unknown bioactivity were identified based upon their ability to selectively inhibit HPV infection at least 1.7 fold (range 2% to 60% infectivity/viability) at the 3 uM HTS standard concentration. These compounds are listed in Table 1.

TABLE 1

Top 104 compounds identified in Primary HTS for HPV microbicides

| Object ID | Infectivity (SEAP Activity) | Viability (CelTiter Glow) | Infectivity vs. viability | IUPAC Name |
| --- | --- | --- | --- | --- |
| 5926288 | 1.52% | 63.27% | 2.40% | N-[(8-hydroxy-7-quinolinyl)(3-nitrophenyl)methyl]butanamide |
| 5929288 | 1.44% | 59.84% | 2.41% | N-[(8-hydroxy-7-quinollnyl)(4-methoxyphenyl)methyl]-2-phenylacetamide |
| 5197089 | 2.01% | 67.01% | 2.99% | N-{[(2-hydroxy-4-nitrophenyl)amino]carbonothioyl}-1-adamantanecarboxamide |
| 5868253 | 4.97% | 66.79% | 7.45% | 5-(3-chloro-4-isopropoxy-5-methoxybenzylidene)-2-thioxo-1,3-thiazolidin-4-one |
| 6190827 | 19.07% | 129.71% | 14.70% | methyl 4-(6-bromo-1,3-benzodioxol-5-yl)-2-methyl-5-oxo-4,5-dihydro-1H-indeno[1,2-b]pyridine-3-carboxylate |
| 5658856 | 14.43% | 75.72% | 19.06% | 8-chloro-4-(3-nitrophenyl)-3a,4,5,9b-tetrahydro-3H-cyclopenta[c]quinoline |
| 5826431 | 19.70% | 100.59% | 19.58% | 1-hydroxy-3-methylpyrido[1,2-a]benzimidazole-4-carboxylic acid |
| 5963375 | 14.20% | 70.35% | 20.19% | 2-({[(3,4-dichlorophenyl)amino]carbonyl}amino)benzoic acid |
| 5379458 | 20.84% | 102.60% | 20.31% | 2-methyl-N-(1-phenylethyl)imidazo[1,2-a]pyridine-3-carboxamide |
| 5345246 | 22.86% | 107.76% | 21.21% | 3,5-dimethyl-1-(2-methylbenzoyl)piperidine |
| 6228481 | 21.82% | 102.16% | 21.35% | N-(5-chloro-2-pyridinyl)-2-[(5-propyl-5H-[1,2,4]triazino[5,6-b]indol-3-yl)thio]butanamide |
| 6013991 | 28.33% | 131.57% | 21.53% | 5-{4-[(5-nitro-2-pyridinyl)oxy]benzylidene}-2-thioxo-1,3-thiazolidin-4-one |
| SPB 04406 | 21.43% | 99.07% | 21.63% | 3-(4-chlorophenyl)-6-(trifluoromethyl)-3H-imidazo[4,5-b]pyridine-2-thiol |
| 6164172 | 22.85% | 93.38% | 24.47% | ethyl 3-(7-hydroxy-3,5-dimethyl-2-phenylpyrazolo[1,5-a]pyrimidin-6-yl)propanoate |
| SPB 01290 | 22.58% | 90.43% | 24.97% | 5-[(3,5-dichlorophenoxy)methyl]-1,2-oxazole-3-carbohydrazide |
| 6172721 | 24.21% | 95.44% | 25.37% | 5-{5-bromo-2-[(2-chlorobenzyl)oxy]benzylidene}-2-thioxo-1,3-thiazolidin-4-one |
| 5914317 | 26.82% | 100.97% | 26.57% | 4-[(dimethylamino)sulfonyl]-N-(1-ethyl-2-oxo-1,2-dihydrobenzo[cd]indol-6-yl)benzamide |
| 5650630 | 26.37% | 93.81% | 28.11% | N-[2-(2-bromophenyl)-1,3-benzoxazol-5-yl]-4-ethoxybenzamide |
| 6077076 | 20.94% | 74.44% | 28.14% | 1-(4-chlorobenzyl)-3-(4-methylphenyl)-1H-pyrazol-5-amine |
| 6138893 | 29.92% | 105.18% | 28.45% | 2-(benzylamino)-1-(4-bromophenyl)-1-(4-methoxyphenyl)ethanol |
| 6114935 | 27.70% | 94.40% | 29.35% | N-(1,1-dioxido-2,3-dihydro-3-thienyl)-2,2,2-trifluoro-N-[3-(trifluoromethyl)phenyl]acetamide |
| 6040256 | 29.61% | 97.48% | 30.38% | N-(4-chlorophenyl)-N'-[5-(1-phenylethyl)-1,3,4-thiadiazol-2-yl]urea |
| 6110323 | 28.40% | 92.86% | 30.58% | (1,1-dioxido-2,3-dihydro-3-thienyl)[3-(trifluoromethyl)phenyl]amine |

TABLE 1-continued

Top 104 compounds identified in Primary HTS for HPV microbicides

| Object ID | Infectivity (SEAP Activity) | Viability (CelTiter Glow) | Infectivity vs. viability | IUPAC Name |
|---|---|---|---|---|
| 5581710 | 23.91% | 75.08% | 31.85% | 1-(3,4-dichlorophenyl)-4-(4,5-dimethoxy-2-nitrobenzylidene)-3,5-pyrazolidinedione |
| 6107659 | 22.29% | 67.85% | 32.85% | 2,5-dichloro-N-(2-methyl-3-nitrophenyl)benzenesulfonamide |
| 5860904 | 21.90% | 65.96% | 33.20% | ethyl (2R,3E)-3-[(4-ethylphenyl)methylidene]-1,4-dioxonaphthalene-2-carboxylate |
| 6186930 | 37.86% | 112.84% | 33.55% | N~2~-(3-chloro-4-methoxyphenyl)-N~1~-(4-isopropylphenyl)-N2~-(phenylsulfonyl)glycinamide |
| 5880766 | 31.85% | 91.98% | 34.62% | N-(3-chloro-4-methylphenyl)-4-(4-fluorophenyl)-6-methyl-2-oxo-1,2,3,4-tetrahydro-5-pyrimidinecarboxamide |
| BTB 09390 | 28.94% | 81.23% | 35.63% | N1-(tert-butyl)-3-(5-nitro-2-{[5-(trifluoromethyl)-2-pyridyl]thio}phenyl)acrylamide |
| RF 02710 | 34.56% | 94.91% | 36.42% | 2-hydroxybenzaldehyde N-(4,6-dichloro-1,3-benzothiazol-2-yl)hydrazone |
| 5994189 | 39.80% | 109.14% | 36.46% | 1-(4-methylbenzyl)-4-(methylsulfonyl)piperazine |
| 6060474 | 38.79% | 104.88% | 36.99% | 1'-methyl-1H,1"H-3,3':3',3"-terindol-2'(1'H)-one |
| BTB 00471 | 40.98% | 109.21% | 37.53% | 3-[4-(phenylmethyl)-5-sulfanylidene-1H-1,2,4-triazol-3-yl]piperidin-2-one |
| NRB 00942 | 37.70% | 99.67% | 37.83% | 3-chloro-N-ethyl-2-[4-(ethylsulfamoyl)phenyl]-1-benzofuran-6-sulfonamide |
| 6074705 | 40.76% | 107.45% | 37.93% | 5-(4-fluorophenyl)-N-[3-(1-hydroxyethyl)phenyl]-7-(trifluoromethyl)-4,5,6,7-tetrahydropyrazolo[1,5-a]pyrimidine-2-carboxamide |
| 5867793 | 36.09% | 95.04% | 37.97% | N-(2-benzoyl-4-bromophenyl)-N,4-dimethylbenzenesulfonamide |
| 5715107 | 42.47% | 111.15% | 38.21% | N-[2-(2-chloro-4-fluorophenyl)-1,3-benzoxazol-5-yl]-3-methoxybenzamide |
| 6021688 | 40.18% | 103.92% | 38.66% | 5-(4-bromophenyl)-N-{3-[(2-methylbenzoyl)amino]phenyl}-2-furamide |
| 6073118 | 36.89% | 92.90% | 39.71% | 3,5-dimethyl-4-[2-(2-methylphenoxy)ethyl]-1H-pyrazole |
| 6070527 | 41.83% | 105.11% | 39.80% | N-(3,4-dichlorophenyl)-N'-{5-[(4-methylphenoxy)methyl]-1,3,4-thiadiazol-2-yl}urea |
| 5976736 | 42.20% | 104.83% | 40.25% | 4-[3-(4-bromophenyl)-5-(7-methyl-2-oxo-1,2-dihydro-3-quinolinyl)-4,5-dihydro-1H-pyrazol-1-yl]-4-oxobutanoic acid |
| 6239347 | 55.08% | 136.02% | 40.50% | 2-(benzoylamino)-6-methyl-4,5,6,7-tetrahydro-1-benzothiophene-3-carboxamide |
| 5143070 | 43.69% | 107.74% | 40.55% | N-[2,2,2-trichloro-1-({[(2-nitrophenyl)amino]carbonothioyl}amino)ethyl]-2-furamide |
| 5740080 | 42.24% | 103.78% | 40.70% | N~1~-(2,6-dimethylphenyl)-N~2~-(4-ethoxyphenyl)-N~2~-{[4-(methylthio)phenyl]sulfonyl}glycinamide |
| 5789300 | 40.11% | 98.40% | 40.76% | N-[5-(4-fluorobenzyl)-1,3,4-thiadiazol-2-yl]-N'-phenylurea |
| 6079458 | 44.08% | 105.15% | 41.92% | 11-(5-methyl-2-thienyl)-3-phenyl-2,3,4,5,10,11-hexahydro-1H-dibenzo[b,e][1,4]diazepin-1-one |
| 5191771 | 39.93% | 95.20% | 41.94% | N-(2-bromo-4-nitrophenyl)-N'-(4-chlorophenyl)urea |
| 6202416 | 51.41% | 122.52% | 41.96% | methyl 4-{3-chloro-4-[(4-nitrobenzyl)oxy]phenyl}-2-methyl-5-oxo-4,5-dihydro-1H-indeno[1,2-b]pyridine-3-carboxylat |
| 5795860 | 47.07% | 111.14% | 42.35% | N-{4-[(4-tert-butylbenzoyl)amino]phenyl}-5-chloro-2-methoxybenzamide |
| HTS 04313 | 36.40% | 85.29% | 42.68% | N-(2-chloro-6-phenoxybenzyl)-N'-(4-fluorophenyl)urea |
| 6106063 | 45.56% | 105.06% | 43.37% | N-[4-(aminosulfonyl)benzyl]-3-(dimethylamino)benzamide |
| 5123541 | 47.01% | 105.55% | 44.53% | N-(3-anilino-2-quinoxalinyl)benzenesulfonamide |
| 5794700 | 49.18% | 109.13% | 45.07% | 2-[(2-fluorobenzoyl)amino]-N-(2-phenylethyl)-5,6,7,8-tetrahydro-4H-cyclohepta[b]thiophene-3-carboxamide |
| NRB 00571 | 49.32% | 108.49% | 45.46% | 6-(acetyloxy)tricyclo[6.2.2.0~2,7~]dodeca-2(7),3,5,9-tetraen-3-yl acetate-[(3-fluorophenyl)amino]-3-methylpyrido[1,2-a]benzimidazole-4-carbonitrile |
| 5873417 | 46.16% | 101.39% | 45.53% | 2-chloro-N-ethyl-N-phenylbenzamide |
| 5272305 | 47.42% | 103.99% | 45.61% | N, N'-[[(4-fluorophenyl)methylene]bis(2,6-dimethyl-4,1-phenylene)]dibenzamide |

TABLE 1-continued

Top 104 compounds identified in Primary HTS for HPV microbicides

| Object ID | Infectivity (SEAP Activity) | Viability (CelTiter Glow) | Infectivity vs. viability | IUPAC Name |
|---|---|---|---|---|
| 5367380 | 50.98% | 109.61% | 46.51% | 5-[4-(4-chlorobenzoyl)-1-piperazinyl]-N-[2-(3,4-dimethoxyphenyl)ethyl]-2-nitroaniline |
| 6144357 | 39.47% | 84.61% | 46.65% | 3-[4,8,11-tri(2-cyanoethyl)-1,4,8,11-tetraazacyclotetradecanyl]propanenitrile |
| JFD 02931 | 46.66% | 99.91% | 46.70% | N~1~-(3-bromophenyl)-N~-2~-(4-chlorophenyl)-N~2~-(methylsulfonyl)glycinamide |
| 6218383 | 47.40% | 101.05% | 46.91% | 2-(2-methoxyphenyl)-N'-{[(4-methylphenoxy)acetyl]oxy}ethanimidamide |
| 6084167 | 53.78% | 113.97% | 47.19% | 1-(4-tert-butylphenyl)-3-(6-methylpyridin-2-yl)urea |
| HTS 07022 | 43.84% | 92.81% | 47.24% | 5-(1,3-benzodioxol-5-yl)-1-(4-fluoro-3-nitrophenyl)-1H-1,2,4-triazole |
| 6033199 | 50.61% | 105.60% | 47.93% | N-butyl-5-(4-ethoxyphenyl)-7-methylpyrazolo[1,5-a]pyrimidine-2-carboxamide |
| 6070486 | 54.56% | 112.90% | 48.33% | 6-chloro-1,3-benzothiazol-2-amine |
| BTB 04800 | 36.37% | 75.00% | 48.50% | 3-chloro-4-ethoxy-N-[2-(2-fluorophenyl)-1,3-benzoxazol-5-yl]benzamide |
| 6021315 | 46.98% | 96.31% | 48.78% | N-{5-[(4-chlorophenoxy)methyl]-1,3,4-thiadiazol-2-yl}-N'-phenylurea |
| 6072068 | 54.52% | 111.75% | 48.79% | 1-(2-fluorophenyl)-2-thioxo-5-[(1,2,5-trimethyl-1H-pyrrol-3-yl)methylene]dihydro-4,6(1H,5H)-pyrimidinedione |
| 6166672 | 53.45% | 108.70% | 49.17% | 10-(2-hydroxyethyl)-2,3,6,7-tetrahydro-1H,5H,11H-pyrano[2,3-f]pyrido[3,2,1-ij]qu inolin-11-one |
| 6105180 | 56.93% | 115.06% | 49.48% | 3-(3-bromo-4-methoxyphenyl)-N-(4-chloro-2,5-dimethoxyphenyl)acrylamide |
| 5944623 | 48.77% | 98.48% | 49.52% | N-(3-methoxyphenyl)-4-methyl-3-nitrobenzamide |
| 5352239 | 43.04% | 86.77% | 49.60% | 2-benzylidene-6-(morpholinomethyl)cyclohexan-1-one hydrochloride |
| NRB 01540 | 50.54% | 101.21% | 49.93% | 4-(3-methylbenzylidene)-1-phenyl-3,5-pyrazolidinedione |
| 6233808 | 58.55% | 116.56% | 50.23% | N-(3-{[(2-chlorophenoxy)acetyl]amino}phenyl)-3-methylbenzamide |
| 6126189 | 49.81% | 99.13% | 50.25% | 4-(4-chloro-3-nitrobenzylidene)-1-(3,4-dichlorophenyl)-3,5-pyrazolidinedione |
| 5585119 | 54.37% | 107.73% | 50.47% | 3-(1-naphthylmethoxy)propanenitrile |
| 5102121 | 55.81% | 110.30% | 50.60% | 2,4,7-trimethylbenzo[b]-1,8-naphthyrid in-5-amine |
| 5947488 | 34.65% | 67.96% | 50.99% | N-1,3-benzodioxol-5-yl-2-[(5-nitro-1H-benzimidazol-2-yl)thio]acetamide |
| 5349092 | 52.52% | 102.70% | 51.14% | N-(2-methoxy-4-{[(2-methylphenoxy)acetyl]amino}phenyl)-2-furamide |
| 6113090 | 55.01% | 106.10% | 51.85% | (4-chlorophenyl)-[2-(3-dimethylamino-1-hydroxypropa-1,2-dienyl)phenyl]methanone |
| BTB 08556 | 55.26% | 106.28% | 52.00% | 2-(4-fluorophenyl)-N-(4-methylphenyl)acetamide |
| 5585700 | 55.38% | 105.40% | 52.54% | N-(5-chloro-2-methylphenyl)-4-methoxybenzenesulfonamide |
| 6118535 | 39.03% | 73.90% | 52.81% | N-{4-[(3-ethoxybenzoyl)amino]-2-methoxyphenyl}-2-furamide |
| 6113089 | 54.57% | 103.13% | 52.91% | 5-chlorothiophene-2-carbaldehyde oxime |
| SEW 06085 | 54.87% | 103.13% | 53.21% | N-[2-(acetylamino)phenyl]-2-iodobenzamide |
| 6168016 | 57.03% | 106.21% | 53.69% | N-(4-nitrophenyl)-N'-(2-pyridinylmethyl)ethanediamide |
| 6198885 | 57.53% | 106.97% | 53.79% | N-(2-bromo-5-{[(4-chloro-2-methylphenoxy)acetyl]namino}phenyl)benzamide |
| 6016344 | 51.43% | 94.63% | 54.35% | N~1~,N~2~-bis(2,5-dimethoxyphenyl)-N~2~-(methylsulfonyl)glycinamide |
| 6167601 | 59.10% | 108.66% | 54.39% | methyl N-(2-ethylphenyl)-N-(methylsulfonyl)glycinate |
| 6226431 | 62.80% | 113.71% | 55.23% | 3-(4-chlorophenyl)-5-(3-hydroxybenzylidene)-2-thioxo-1,3-thiazolidin-4-one |
| 5851060 | 56.29% | 101.76% | 55.31% | S-[3-(8-methyl-1,2,3a,4,5,6-hexahydro-3H-pyrazino[3,2,1-jk]carbazol-3-yl)-3-oxopropyl]ethanethioate |

TABLE 1-continued

Top 104 compounds identified in Primary HTS for HPV microbicides

| Object ID | Infectivity (SEAP Activity) | Viability (CelTiter Glow) | Infectivity vs. viability | IUPAC Name |
|---|---|---|---|---|
| 5915049 | 56.77% | 101.60% | 55.87% | N-[(2-bromophenyl)(phenyl)methyl]urea |
| 5571356 | 59.08% | 105.53% | 55.98% | 2-(4-chloro-3,5-dimethylphenoxy)-N-[3-chloro-4-(4-morpholinyl)phenyl]acetamide |
| 6013775 MWP | 58.77% | 104.85% | 56.05% | 1-furan-2-yl-3-[4-(trifluoromethyl)phenyl]sulfanylpropan-1-one |
| 01152 | 57.82% | 103.08% | 56.09% | 1-(2-tert-butyl-2-methylcyclopropyl)-1-ethanone semicarbazone |
| 5104160 | 63.03% | 112.10% | 56.23% | 5-[4-(benzyloxy)-3,5-dichlorobenzylidene]-2-thioxo-1,3-thiazolidin-4-one |
| 6142367 | 61.22% | 105.71% | 57.92% | 2-{5-[3-(methoxycarbonyl)-2-methyl-5-oxo-4,5-dihydro-1H-indeno[1,2-b]pyridin-4-yl]-2-furyl}benzoic acid |
| 6177037 | 63.98% | 109.51% | 58.43% | (2' 2-dimethyl-5-nitro-1,3-dioxan-5-yl)methyl |
| 5893711 | 63.26% | 107.87% | 58.65% | [3,5-bis(methylthio)-4-isothiazolyl]carbamate |
| 6058136 | 64.68% | 109.35% | 59.15% | N-[2-(benzoylamino)benzoyl]phenylalanine |
| 6156840 | 63.49% | 107.27% | 59.19% | 2-(3-fluorophenyl)-5,6-dimethylpyrazolo[1,5-a]pyrimidin-7-ol |
| 5896361 | 60.83% | 102.50% | 59.34% | 1,4-dimethoxy-1,4-dihydro-2,3-quinoxalinedione |
| 5842264 | 67.04% | 112.51% | 59.58% | 4-(1,3-dioxo-1,3-dihydro-2H-isoindol-2-yl)-N-(4-methyl-2-pyrimidinyl)benzenesulfonamide |
| 6137315 | 55.92% | 93.71% | 59.67% | 3-chloro-1-(2,4-dimethylphenyl)-4-[(3,4-dimethylphenyl)amino]-1H-pyrrole-2,5-dione |
| 6001901 | 65.81% | 109.77% | 59.95% | 3-{[(2-hydroxy-1-naphthyl)methylene]amino}-2-methyl-4(3H)-quinazolinone |

Identification of lead compounds from libraries of compounds of unknown bioactivity. The lead compounds of unknown bioactivity were retested in the primary screen assay and in a secondary screen assay in which we monitored infectivity in 293T cells using an HPV16 pseudovirus that has a different reporter gene, *renilla* luciferase, expressed behind a different promoter (HPV16 promoter). Twenty-two of the 78 compounds were selected for further analyses (Table 2) based upon their having been reproducibly effective at inhibiting HPV16 pseudovirus infectivity.

All but one of these compounds (6 is longer commercially available) were repurchased and subjected to a tertiary screen performed in the human keratinocyte cell line, HaCaT, and using HPV16 pseudoviruses encoding a third reporter gene, firefly luciferase, transcribed from a different, E1a, promoter.

In this assay, dose response curves were performed at seven concentrations of compound ranging from 0.1 to 100 uM, and both the efficiency of inhibition of infectivity as well as cell viability were assayed.

The infectivity assay was repeated at least twice and each assay was performed in replicate (n≥3). Results for representatives experiments are shown in FIG. 2. Two compounds, 13 and 14, stood out both in terms of displaying submicromolar $IC_{50}$ (for compound 13=0.8 uM; for compound 14=0.2 uM) and little to no cytotoxicity ($CD_{50}$ for compound 13=25 uM, $CD_{50}$ for compound 14>100 uM). Several others, (compound 9, 12, 20-22) also showed $IC_{50}$ in the low to mid uM range, with acceptable cytotoxicity properties (i.e. $CD_{50}$ greater than 10× their $IC_{50}$).

TABLE 2

| | | Primary HTS | | Secondary screening | | | | Luciferase assay | |
|---|---|---|---|---|---|---|---|---|---|
| Compound ID | Object ID | SEAP vs Viability | Viability % Average | SEAP vs Viability | Viability % Average | SEAP vs Viabilty | Viability % Average | RL % Average | Viability % Average |
| 001 | 6164172 | 13.07% | 85.00% | 32.62% | 101.76% | 30.63% | 73.38% | 64.85% | 91.76% |
| 002 | 5826431 | 13.52% | 83.47% | 25.87% | 117.70% | 36.82% | 94.61% | 75.09% | 88.63% |
| 003 | 5379458 | 18.68% | 105.26% | 23.00% | 99.94% | 26.48% | 85.27% | 71.67% | 103.23% |
| 004 | SPB 01290 | 18.30% | 94.54% | 26.86% | 86.32% | 14.42% | 97.26% | 68.26% | 86.24% |
| 005 | 5345246 | 29.51% | 101.84% | 16.20% | 113.69% | 42.55% | 84.82% | 102.39% | 95.25% |
| 006 | 5914317 | 24.35% | 89.80% | 29.30% | 112.14% | 77.63% | 104.62% | 71.67% | 92.74% |
| 007 | 6073118 | 31.99% | 82.55% | 41.80% | 103.26% | 36.34% | 84.43% | 68.26% | 79.65% |
| 008 | 6114935 | 37.28% | 96.43% | 18.12% | 92.37% | 50.05% | 110.13% | 177.47% | 92.68% |
| 009 | 6138893 | 16.47% | 101.10% | 43.38% | 109.27% | 48.71% | 102.07% | 71.67% | 99.03% |
| 010 | 6060474 | 34.36% | 86.94% | 43.23% | 122.82% | 69.69% | 89.11% | 30.72% | 48.79% |
| 011 | 6190827 | 17.74% | 86.95% | 20.39% | 172.46% | 64.77% | 97.27% | 95.56% | 95.74% |
| 012 | 6013991 | 39.41% | 85.83% | 17.25% | 177.32% | 81.03% | 82.40% | 105.80% | 107.21% |
| 013 | 6228481 | 8.25% | 90.79% | 35.38% | 113.54% | 98.12% | 111.13% | 150.17% | 118.34% |
| 014 | 5367380 | 65.38% | 98.02% | 36.58% | 121.20% | 71.34% | 106.27% | 37.54% | 105.54% |
| 015 | 5650630 | 11.09% | 89.55% | 41.64% | 98.06% | 40.21% | 95.74% | 102.39% | 97.74% |
| 016 | 6110323 | 36.15% | 98.16% | 20.65% | 87.57% | 59.79% | 104.09% | 146.76% | 95.85% |
| 017 | 5352239 | 32.86% | 71.47% | 53.22% | 102.06% | 41.61% | 89.90% | 92.15% | 84.51% |
| 018 | 6172721 | 27.21% | 87.75% | 21.22% | 103.14% | 73.84% | 105.85% | 112.63% | 112.92% |
| 019 | 6074705 | 49.98% | 115.53% | 31.54% | 99.37% | 44.33% | 91.90% | 88.74% | 107.01% |

TABLE 2-continued

| Compound ID | Object ID | Primary HTS | | Secondary screening | | | | Luciferase assay | |
|---|---|---|---|---|---|---|---|---|---|
| | | SEAP vs Viability | Viability % Average | SEAP vs Viability | Viability % Average | SEAP vs Viabilty | Viability % Average | RL % Average | Viability % Average |
| 020 | SPB 04406 | 20.95% | 95.84% | 21.90% | 102.31% | 52.32% | 113.62% | 109.22% | 89.54% |
| 021 | HTS 07022 | 34.20% | 92.82% | 53.48% | 92.80% | 44.42% | 116.12% | 109.22% | 99.66% |
| 022 | 6079458 | 45.21% | 89.19% | 42.95% | 121.10% | 86.31% | 93.74% | 44.37% | 97.27% |

The 21 selected compounds were also tested for their ability to inhibit infection by bonafide HPV16 in 293T cells by measuring early viral gene expression by real time PCR at 48 hours post infection (FIG. 3) after treatment of the cell with 5 to 10 uM of each compound. Consistently with the data of reporter gene assays, HPV early gene expression was inhibited by Compounds 4, 13, 14, 18 and 20. Given the large differences in $IC_{50}$ and $CD_{50}$, and the reproducible capacity to inhibit infection by HPV16 pseudovirus and HPV16 virus in different cell types, Compounds 13 and 14 were selected for further analysis.

Compounds 13 and 14: inhibition of infection by multiple papillomavirus genotypes. The goal of this study is to identify compounds that inhibit all sexually transmitted HPVs. For this reason, we monitored the ability of Compounds 13 and 14 to inhibit infection of two additional papillomavirus pseudoviruses that were generated using the capsid proteins of two other sexually transmitted HPVs, high risk HPV31 and low risk HPV11.

These pseudoviruses have encapsidated in them the same reporter plasmid used in our HPV16 pseudovirus-based secondary screen (FIG. 2). HPV11 and 31 were both efficiently inhibited by Compounds 13 and 14 (FIG. 4). Compound 13 gave $IC_{50}$s of <0.1 uM and 0.15 uM for HPV11 and HPV31 pseudoviruses respectively. Compound 14 gave $IC_{50}$s of <0.1 uM for both HPV11 and HPV31 pseudoviruses. HPV11, HPV16, and HPV31 are all sexually transmitted HPVs and belong to both the high-risk (cancer causing—HPV16 and HPV31) as well as low-risk (non cancer causing, responsible for florid disfiguring genital warts—HPV11). The strong inhibition of these three different HPVs indicates that the compounds of the present invention will inhibit all HPV infections given their varied phylogeny.

Figure 6:
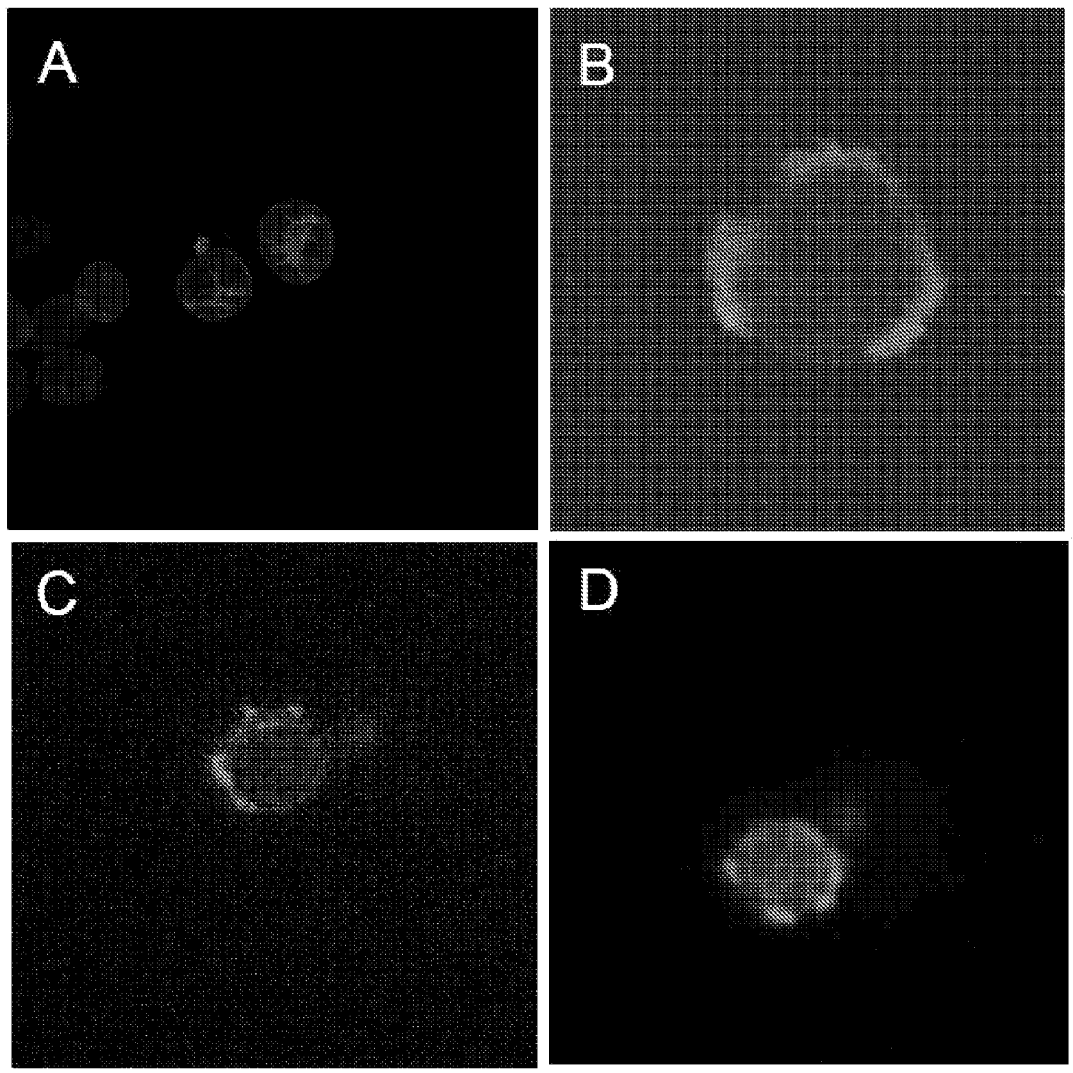
FIG. 6. Localization of HPV16 pseudovirions 24 hours post infection. Shown are representative confocal images of cells exposed to cyberXX-labeled HPV16 pseudovirus in the absence (FIG. 6B) or presence of Compound 13 (FIG. 6C) and Compound 14 (FIG. 6D).

Mechanism of action of Compounds 13 and 14. To begin to assess the mechanism by which Compounds 13 and 14 inhibit HPV infection, we performed fluorescent microscopy studies on cells treated or not treated with Compounds 13 and 14 that were exposed to HPV16 pseudoviruses in which the encapsidated DNA was labeled with a fluorescent intercalating agent. As shown in FIG. 6, HPV16 pseudoviruses were able to enter cells treated with either compound indicating that they function post-entry. At 24 hours post infection we observed a typical perinuclear staining for the fluorescently labeled HPV16 pseudoviruses in both the untreated and drug treated cells.

Discussion

Microbicides that can inhibit infection by sexually transmitted HPVs may provide a new means for reducing the risk to women of infection by these common pathogens that are the most frequent cause of STDs and are the etiological agent for many anogenital cancers including cervical cancer. In this study we describe the use of a robust HTS that led to the identification of two strong inhibitors of HPV infection that have favorable therapeutic indices, Compounds 13 and 14 (see FIG. 7 for structure). Both compounds can inhibit the infection by multiple anogenital HPVs and do so at the post-entry level.

Materials and Methods

Primary High Throughput Screen: Using a Biomek FX Workstation (Beckman-Coulter, Inc.), 293T cells were plated in 384 well plates at a count of 15,000 cells per well in 50 µL of complete growth medium. After incubation at 37° C. for 24 hrs, 35 µL of media was removed. Library compounds dissolved in DMSO were added to each well at a final concentration of 3.3 µM. Following 4 hr incubation in 37° C. in the presence of a compound, 40 viral genome equivalents per cell (vge/cell) of pseudovirions containing pSEAP2-control were added to each well. Cells were incubated at 37° C. for 48 hrs. 2.5 µL of media was collected for SEAP assay using a PHOSPHA-LIGHT chemiluminescent alkaline phosphatase assay (Applied Biosystems). Cell viability was determined using the CellTiter Glo Luminescent Cell Viability Assay™ (Promega).

To identify specific chemical inhibitors of HPV infection, we performed a HTS of over 40,000 small molecules including 16,000 compounds from ChemBridge DIVERSet collection, 14,400 compounds from the Maybridge HitFinder library, 5,000 known bioactive compounds from NIH and from the Prestwick Chemical Library, and a number of compounds from smaller libraries available at the UW/Keck small molecule screening facility. A Z-Score [Zhang, J. H., et al., *J. Biomol Screen*, 1999, 4(2):67-73] and a coefficient of variation (CV) of each screening plate were calculated to verify screening reliability. Plates with a Z-score less than 0.5 or CV greater than 20% were excluded and were rescreened.

Secondary Screen: In 96-well plates, 293T cells were plated at a count of 60,000 cells per well and HaCaT cells were plated at a count of 20,000 cells per well. 293T cells were screened with both pSEAP2-control packaged pseudovirions, while inhibition was confirmed in HaCaT using HPV16wpA-RL packaged pseudovirions. The protocol for the secondary screen was identical to that of the primary screen with the exception that all volumes were scaled up by a factor of four. RL activity was measured using the *Renilla* Luciferase Assay System (Promega).

To eliminate any cytotoxic compounds or compounds with inconsistent effects, the primary hits were screened again in 293T cells using pSEAP2-control containing pseudovirions. Quality control of screening was maintained by excluding and re-screening any plate with a Z-score less than 0.5 or CV greater than 20%. Observation of significant cell death or cell viability data was used to eliminate cytotoxic compounds.

Tertiary Screen: In 96-well plates, HaCaT cells were plated at a count of 10,000 cells per well 24 hours prior to the assay. At 4 hours prior to exposure of cell to pseudoviruses, compounds were added to plates in 1% DMSO final concentration at the indicated amounts. Four hours later, 10 multiplicity of infection (M.O.I) units of HPV16 pseudovirus carrying the plasmid LucF was added to the cells. 72 hours later, cells were lysed and luciferase assays performed using the Luciferase Assay System (Promega Cat. #E1501). For infection studies with HPV11 and HPV31 pseudoviruses, 200 virus genome equivalents (vge) of virus per cell were used. Cell viability was assessed in parallel plates by Luminescent Cell Viability Assay (Promega Cat. #G7571).

Wild Type HPV16 Infection: 293T cells were plated at a count of 600,000 cells per well in 6-well plates. The infection protocol was identical to that used for the secondary screen except volumes were scaled up by a factor of 10. After 2 day infection, total RNA was isolated from infected cell lysate and treated with DNase I (Promega) as previously. (Pyeon, D. et al., Establishment of human papillomavirus infection requires cell cycle progression, PLos Pathog. 2009 February; 5(2):e1000318. Epub 2009 Feb. 27). Complementary DNA (cDNA) was synthesized from the normalized total RNA with the SuperScript cDNA synthesis kit (Invitrogen). All oligonucleotide primers (0.5 μM) for PCR are previously published (Pyeon D. et al., Production of infectious human papillomavirus independently of viral replication and epithelial cell differentiation, Proc. Nat'l Acad. Sci. USA, 2005 Jun. 28; 102(26):9311-6, Epub 2005 Jun. 15) or listed in Table 2.

Conventional PCR was performed with Taq DNA polymerase (Promega) and the following cycle: denaturation at 94° C. for 5 min, 42 cycles of 94° C. for 30 sec., 55° C. for 1 min., and 72° C. for 1 min., followed by extension at 72° C. for 7 min. Final products were analyzed by 1% agarose gel electrophoresis and ethidium bromide staining. Quantitative RT-PCR was performed using QuantiTect SYBR green PCR kit (Qiagen) with the following cycle: denaturation at 95° C. for 5 min. and 40 cycles of 95° C. for 30 sec., 55° C. for 30 sec., and 72° C. for 30 sec.

Virus particle sub cellular localization studies: A target DNA was labeled with Syto-14 (Invitrogen, 25 μM) in 293FT cells before virus was being packaged. HaCaT cells were infected with the labeled HPV pseudovirus for 24 hours, harvested, and fixed with 1% formaldehyde for 30 minutes, followed by permeabilization with 0.2% Triton X-100 for 10 minutes. Cells were blocked with Image-IT FX Signal Enhancer (Invitrogen) for 30 minutes and incubated with rabbit anti-lamin B1 (ab16048, Abcam) antibodies. Subsequently, cells were incubated with Alexa 568 anti-rabbit IgG for 30 minutes and mounted with Prolong Gold anti-fade mounting solution (Invitrogen). Virus localization was determined by fluorescence.

EXAMPLE II

Six to eight week old virgin mice (FVB/N strain) were treated four days before infection with Depoprovera (3 mg, subcutaneously injected in phosphate buffered saline), a synthetic progesterone to synchronize the mice in diestrus. Six hours before infection, mice were treated topically with Conceptrol (50 ul delivered intravaginally). Four hours before infection mice were treated topically with compound 13 (5 mM final concentration) or vehicle only (PEG400 in aqueous solution) by administering 50 ul intravaginally.

Figure 10:
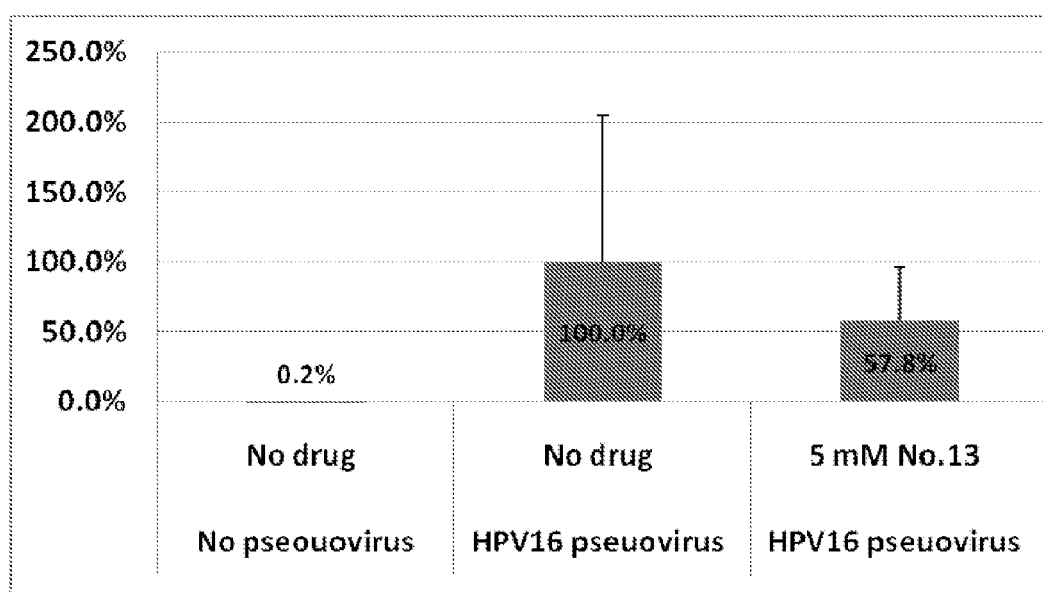
FIG. 10. Infectivity of HPV16 pseudovirus carrying luciferase reporter gene exposed to mouse female reproductive tract epithelia that were not exposed to any microbicide or exposed to 5 mM compound 13.

At 0 hours, $7.5 \times 10^6$ pseudoviruses (HPV16 L1/L2 virus like particles containing a plasmid expressing firefly luciferase) were delivered intravaginally in the same vehicle with or without an additional drug (same concentration). A third administration of drug or vehicle was given four hours following infection. Lower reproductive tracts were harvested 72 hours post-infection, protein lysates made, and luciferase assays carried out, which were corrected for protein concentration in each sample. FIG. 10 shows the results of this study. Each experimental group had four mice.

We claim:

1. A method of treating human papillomavirus (HPV) infection, comprising the step of exposing tissues or cells susceptible to post-entry HPV infection to an effective amount of a compound having a formula of Compound 13:

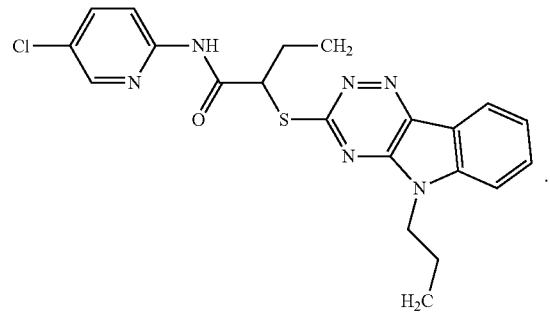 [SMILES: CCCn1c2ccccc2c2nnc(SC(CC)C(=O)Nc3ccc(Cl)cn3)nc21]

2. The method of claim 1 wherein the HPV is a high risk HPV selected from the group consisting of HPV16, HPV18, HPV31, HPV33, HPV35, HPV39, HPV45, HPV51, HPV52, HPV56, HPV58, HPV59, HPV66, and HPV68.

3. The method of claim 1 wherein the HPV is a low risk HPV selected from HPV6 and HPV11.

4. The method of claim 1 wherein the tissue or cells are selected from the group consisting of vulvovaginal tissues and cells and rectal tissue and cells.

5. The method of claim 1 wherein the tissue or cells are selected from the group consisting of oral cavity tissue and cells and oral pharynx tissue and cells.

6. The method of claim 1 wherein an effective amount of Compound 13 is in the range of 0.1 uM to 100 mM.

7. The method of claim 1 wherein an effective amount of Compound 13 is in the range of 1 mM to 10 mM.

* * * * *

UNITED STATES PATENT AND TRADEMARK OFFICE
CERTIFICATE OF CORRECTION

| | | |
|---|---|---|
| PATENT NO. | : 9,066,951 B2 | Page 1 of 1 |
| APPLICATION NO. | : 12/994592 | |
| DATED | : June 30, 2015 | |
| INVENTOR(S) | : Paul F. Lambert et al. | |

It is certified that error appears in the above-identified patent and that said Letters Patent is hereby corrected as shown below:

In The Specification

Column 4, line 13 - (U) should be --(II)--

Signed and Sealed this
Sixteenth Day of August, 2016

Michelle K. Lee
*Director of the United States Patent and Trademark Office*